United States Patent [19]
Orth et al.

[11] Patent Number: 5,981,173
[45] Date of Patent: Nov. 9, 1999

[54] GENITAL HUMAN PAPILLOMAVIRUS TYPE 68A (HPV-68A), RELATED TO THE POTENTIALLY ONCOGENIC HPV-39

[75] Inventors: Gerard Orth, Sceaux, France; Sylvie Beaudenon, Highland Park, N.J.; Michele Longuet, Palaiseau, France

[73] Assignees: Institut Pasteur; Institut Nationale de la Sante Et de la Recherche Medicale, both of Paris, France

[21] Appl. No.: 08/815,667

[22] Filed: Feb. 11, 1997

Related U.S. Application Data

[60] Provisional application No. 60/011,650, Feb. 14, 1996, and provisional application No. 60/020,458, Feb. 15, 1996.
[51] Int. Cl.$^6$ .............................. C12Q 1/70; C12P 19/34; A61K 39/12; C12N 15/34
[52] U.S. Cl. .................................. 435/5; 435/6; 435/7.1; 435/320.1; 435/91.1; 536/23.72; 424/204.1; 424/229.1; 424/199.1
[58] Field of Search ............................. 424/199.1, 204.1, 424/229.1; 536/23.72; 435/5, 6, 7.1, 320.1, 91.1

[56] References Cited

PUBLICATIONS

Volpers et al, 1991, Virology, vol. 181, pp. 419–423 1991.
Reuter et al, 1991, Journal of Virology, vol. 65, No. 10, pp. 5564–5568.
Longuet et al, 1996, Journal of Clinical Microbiology, 1996, vol. 34, No. 3, pp. 738–744.

*Primary Examiner*—Mary E. Mosher
*Assistant Examiner*—Ali R. Salimi
*Attorney, Agent, or Firm*—Finnegan, Henderson, Farabow, Garrett & Dunner, L.L.P.

[57] ABSTRACT

The genomes of two novel human papillomavirus (HPV) types, HPV68 and HPV70, were cloned from a low grade cervical intraepithelial neoplasia and a vulvar papilloma, respectively, and sequenced. Both types are related to HPV39, a potentially oncogenic virus. HPV68 and HPV70 were also detected in genital intraepithelial neoplasia from three patients and one patient, respectively. Comparison with sequence data in the literature indicates that the subgenomic ME180-HPV DNA fragment, cloned from a carcinoma cell line, corresponds to an HPV68 subtype and that several HPV DNA fragments amplified by PCR from genital neoplasia represent worldwide distributed variants of HPV68 and HPV70.

13 Claims, 9 Drawing Sheets

HPV 68E

AACGGCTTTAGGCATAAAGTTTAACTGTTTTGGCTTGCCTAATAGCATAGTTGGCCAGTATAACTACTT
TTGCATTCAAGAATCTGTCTGGTAGTGTAAGTTATACAGTTGACTAATACTACATCCATAAATTTGTGCA
ACCGAAAAAGGTTGGGCACACATACCAATACTTTTACTTATAACATTTTACAATTATTCTATATAAAAA
AAGGGTGGGACCGAAAACGGTCACGACCCGAAAACGTGTATATAAAGCTGAACACACAGCAGTTCTA
TACTAATGGCGCTATTTCACAACCCTGAGGAACGGCCATACAAATTGCCAGACCTGTGCAGGACATTG
GACACTACATTGCATGACGTTACAATAGACTGTGTCTATTGCAGAAGGCAACTACAACGGACAGAGGT
ATATGAATTTGCCTTTAGTGACCTATGTGTAGTGTATAGAGACGGGTACCATTTGCTGCATGCCAATC
ATGTATTAAATTTTATGCTAAAATACGGAACTACGATATTACTCGGAATCGGTGTATGCAACTACATT
AGAAACCATAACTAATACAAAGTTATATATAATTTATTGATAAGGTGCATGAGTTGCCTGAAACCATTGT
GTCCAGCAGAAAAACTAAGGCACCTAACACAAACGAAGATTACAATAAAATAGCAGGAAACTTTAC
AGGACAGTGTCGGCACTGCTGGACCAGTAAGCCCACCGTGCAGGAAATTGTGTTAGAGCTATGTCCATACAA
GTTTAAGTAACTATGCATGGACCTTGTGACCCTTGTATGTCACGAGCAATTCAGACGATGAATAGATGAAC
TGAAATACAGCCGGTTGACCCTTGTATGTCACGAGCAATTCAGACGGGACGAACAACAGCGTCACAGA
CCGACCATGCAGTTAATCACCAACATCTACTACTAGCCAGACTAGTAGTAGAAGCGTCGCGGACAACCT
ATTCAGTGTCTGTGTAAGTGTAACAAGGCACTCAACAAGGCACTCAACTAAATTTGTGTCCGTGGTGTGCAACTGAAACCC
GCGGACACTACAACAGCTGTTTATGGACTCACTAAATTTGTGTCCGTGGTGTGCAACTGAAACCC
AGTAA (SEQ ID NO: 12)

HPV68 L

ATGGCATTGTGGCGAGCTAGCGACAACATGGTGTATTTGCCTCCCCCTCAGTGGCGAAGGTTGTC
AATACAGATGATTAGTGACACGCCACTGGCATTACTATGTGGTACATCTAGGTTATTAACT
GTAGGCCATCCATATTTAAGGTTCCTATGTCTGGGCCGCAAGCCAGGGCATTCCTAAGGTGTCT
GCATATCAATACAGAGTGTTTAGGGTTACCTTACCTGATCCTAATAAATTTAGTGTTCCTGAGTCTA
CATTATATAATCCAGATACACAGCGCATGGTATGGGCCTGTGTTGGTGTTGAAATAGGTAGGGGC
AGCCATTGGGCGTTGCCTTAGTGGCATCCACTATATAATAGGCTGGATGATACTGAAAATTCCC
CGTTTCCTCTAATAAAATCCTAAAGACAGTAGGACAATGTTGCAGTGGACTGTAAACAAAC
AGCTGTGTATTATAGCTGTGTGTTCCTGCTATTGGCGAGCACTGGGCCAAAGTAAATCTTGTAAGC
CTACCAATGTACAACAAGGGACTGTCCCCCATTGGACTTTGGTACATTACAAGAAAGCGAGGTA
GATATGATTGATACAGGATATGTCAATCTGTTTGTTTACGTAGGAACAGTGTATATTGCAAATGTCTGCAGATGTGTATG
CCTTTGGATATATGTCAATCTGTTTGTTTACGTAGGAACAGTCTATATTGCAAATGTCTGCAGATGTGTATG
GAGACAGTAGTGTTTTTTGTTTACGTAGGAACAGTCTATATTGCCAGGCATTTTTGGAATAGGGAG
GCATGGTAGGGGACACTATTCCCACTGACATGTATATTAAGGCACTGACATTCGTGAAACTCCTA
GTAGTTATGTGTATGCCCCCTAGCGGGTCTATGGTTGTCCTCTGACTCCCAGTTATTTAACAA
GCCCTATTGGCTGCACAAGGCACAGGGACACAACAATGGTATTGTTGTTGGCATAATCAATTATTCT
TACCGTTGTGGATACAACGCGCAGTAATAATTAAGGAATATGTTAGGCATGTTGAGGAATATGATTTGCAGTT
AGCTGTGTATGATTCTTAATAACATTATCCACTGATGTAATGTCATATATACATATGAATCCT
TATATTCAGTGTGTACTATAAACATTATTCCACCATCTGTTGCCCCTCCACCATCTGCTAGTCTTGTAGATACATACC
GCTATTTGGATGATTGGAATTTGGTGTTGCCCTCCACCATCTGCTAGTCTTGTAGATACATACC
GCTACCTACAATCAGCAGCAATTACATGTCAAAAGGACGCCCCTGCACCTGTTAAAAAAGATCCCT
ATGATGGTCTTAACTTTTGGAATGTGGATTTAAAGGAAAAGTTTAGTTCTGAACTGGACCAATTCC
CATTAGGACGCAAATTTCTGTTACAGCCAGGTGTTCGCAGACGCAGTTTAGTGTTCGCAGAGCGCAGGCCCCTCGTAAAC
GCACTGCCACTGCGACTACCACATCTACCTTCTAAACACAAACGTAAACGTGTGTCAAATAA (SEQ ID NO: 13)

HPV 70

```
AAACGTATTCCCTATTTTTTTACAGATGGCTTTGTGGCGGTCTAGTGACAACACGGTGTATTTGCCACC
CCCTTCTGTGGCGAAGGTTGTCAATACAGATGATTATGTAACACGTACAGGCATATATTATTATGCTGG
AACGTCTCGCTTATTAACAGTAGGGCATCCTTATTTTAAGGTACCTGTAAATGGTGGCCGCAAGCAGGA
ATACCTAAGGTGTCTGCATATCAGTATAGGGTATTTAGGGTATCCCTACCTGATCCTAATAAGTTTGG
CCTTCCGGATCCTTCCCTTTATAATCCTGACACACAACGCCTGGTATGGGCCTGTATAGGTGTGGAAAT
TGGTAGAGGCCAGCCATTGGGCGTTGGCGTTAGTGGACATCCTTTATATAATAGGTTGGATGATACTGA
AAATTCTCATTTTTCCTCTGCTGTTAGTACACAGGACAGTAGGGACAATGTGTCTGTGGACTATAAGCA
AACACAGTTATGTATTATAGGCTGTGTTCCTGCTATGGGAGAGCACTGGGCAAAGGGCAAGGCCTGTAA
GTCCACTACTGTACAACAGGGCGATTGTCCACCATTAGAATTAGTTAATACTGCAATTGAGGATGGCGA
TATGATAGATACAGGCTATGGTGCCATGGACTTTCGTACATTGCAGGAAACCAAAAGTGAGGTACCACT
AGATATTTGCCAATCCGTGTGTAAATATCCTGATTATTTGCAGATGTCTGCTGATGTATATGGGGACAG
TATGTTTTTTTGTTTGCGCAAGGAACAGTTGTTTGCCAGGCACTTTTGGAATAGAGGTGGCATGGTGGG
CGACACAATACCTTCAGAGTTATATATTAAAGGCACGGATATACGTGAGCGTCCTGGTACTCATGTATA
TTCCCCTTCCCCAAGTGGCTCTATGGTCTCTTCTGATTCCCAGTTGTTTAATAAGCCCTATTGGTTGCA
TAAGGCCCAGGGACACAATAATGGCATTTGTTGGCATAACCAGTTGTTTATTACTGTGGTGGACACTAC
ACGTAGTACTAATTTTACATTGTCTGCCTGCACCGAAACGGCCATACCTGCTGTATATAGCCCTACAAA
GTTTAAGGAATATACTAGGCATGTGGAGGAATATGATTTACAATTTATATTTCAATTGTGTACTATCAC
ATTAACTGCAGACGTTATGGCCTACATCCATACTATGAATCCTGCAATTTTGGACAATTGGAATATAGG
AGTTACCCCTCCACCATCTGCAAGCTTAGTGGACACGTATAGGTATTTACAATCAGCAGCTATAGCATG
TCAAAAGGATGCTCCTACACCTGAAAAAAGGATCCCTATGACGATTTAAAATTTTGGAATGTTGATTT
AAAGGAAAAGTTTAGTACAGAACTAGATCAGTTTCCTTTGGGGCGCAAATTTTTACTACAGGTAGGGGC
TCGCAGACGTCCTACTATAGGCCCTCGCAAACGCCCTGCGTCAGCTAAATCGTCTTCCTCAGCCTCTAA
ACACAAACGGAAACGTGTGTCCAAGTAATGTATGTATGTGGTATGCTGTGTATTTATGTACTATTACAT
ATTTGTGTTTTATGTGGTATGCTTGCACACTGTTTACATATTTGTGTTTGTATGTGGTATGCTTGCAC
ACTGTACTGTATATGTTTGTCCTGGTACATATTTGTGGTTGTATGTGTATATGTTGCGTGCTATGTGTA
TGTTTTAGAAGTATGTGTGTATGTATGTTTTTGTTAATAAAGTATGTATGGAAGTTTCATTTGTGGTTG
CACCCTGTGACTAAGGTGTTGTCCCTGTTTTACATATAATAGGAGTGTGATTACCAACATTTCCTACAT
AATTTTATGCCCTACCCTAAGGTGTGTGTATACCATCTGTAGTTTATACATTTATATTTTATAGTGGGT
TACCTGTATACAGCAACGGCCATTTTGTGTGAAACCGTTTTCGGTTGCATTTGGCTTTGTACCATCAGT
TACCCTTATAAACCTTTTGTATCAGCAAAAACATGTCCTGTAACCTAAGTTCACCTACATACTTGGCAC
TACTAACAGTTTTAGTGGCGCACCTACACTTAGTCATCATCCTGTCCAGGTGCACTACAACAATGCTTT
GGCAACCTTATGCACCTCCACCCTGTCTAATAAAGTGCTTTTAGGCATGTATTTTACCTGTTTTTACTT
ACCTAATAGCATAGTTGGCCTGTATAACAGCTTTTACATCCAAGAATGTGTCGTTTGGTGCAAGTTATA
TTTTGTGACTAATATTTTTACAGACCTGTGTGCAACCGAAATAGGTTGGGCAGACATTCCTATACTTTT
ACTTATAACATTTTACAATCATAATTTAAAAAAAGGGAGGCACCGAAAACGGTCACGACCGAAAACGGT
GTATATAAAACCATGCAAAAGTTGCTTGCCCATACGGAATGGCGCGATTTCCCAATCCTGCAGAACGGC
CATACAAATTGCCTGACCTGTGCACGGCGCTGGACACTACATTGCACGACATTACAATAGACTGTGTCT
ATTGTAAAACACAGCTACAGCAAACAGAGGTATATGAATTTGCATTTAGTGATTTATTTATAGTATATA
GAAACGGGGAGCCATATGCTGCATGCCAAAAATGTATTAAATTTCATGCTAAAGTAAGGGAACTACGGC
ATTATTCGAACTCGGTGTATGCAACAACTTTGGAAAGCATAACTAATACCAAGTTATATGATTTATCAA
TAAGGTGCATGAGTTGCCTGAAACCATTGTGTCCAGCAGAAAAATTAAGGCATGTTAATACCAAAAGAA
GATTTCACCAAATAGCAGGAAGCTATACAGGACAGTGCCGACACTGCTGGACCAGCAACCGGGAGGACC
GCAGACGTATACGAAGAGAAACACAAGTATAAATATAAATATGCATGGACCACGGCCGACATTGCAAGA
GATTGTTTTAGATTTATATCCATACAATGAAATACAGCCGGTCGACCTTGTATGTCACGAGCAATTAGA
AGATTCAGACAATGAAACAGATGAACCCGACCATGTAGTTAATCACCAACAACAACTACTAGCCAGACG
GGAAGAACCACAGCGTCACAAAATACAGTGTATGTGTTGTAAGTGTAATACTACACTGCACTTAGTAGT
AGAAGCCTCACAAGAGAACCTGCGATCTCTACTGCAGCTGTTTATGGAGACACTGTCATTTGTGTGTCC
CTGGTGTGCATCGGGAACCCAGTAACCTGCAATGGCCAAT (SEQ ID NO: 14)
```

GENITAL HUMAN PAPILLOMAVIRUS TYPE 68A (HPV-68A), RELATED TO THE POTENTIALLY ONCOGENIC HPV-39

This application claims the benefit of the provisional U.S. application serial No. 60/011,650 filed Feb. 14, 1996, and Ser. No. 60/020, 458, filed Feb. 15, 1996.

BACKGROUND OF THE INVENTION

The invention relates to the DNAs of papillomaviruses HPV68 and HPV70 and variants of these papillomaviruses, to immunogenic proteins of these viruses, to expression vectors encoding these proteins, and to products genetically or immunologically related to these papillomaviruses.

More than 30 types of human papillomaviruses (HPVs) infecting the genital tract have been identified so far (7, 17). The expression "papillomavirus" covers a large number of viruses having in common the role of being held responsible for several forms of viral infections ranging from relatively benign warts of the skin and mucous membranes to hyperplasias capable of degenerating into intra-epithelial neoplasias and cutaneous cancers. Among papillomavirus infections, mention should also be made more particularly of cutaneous warts (in particular common warts and plantar warts epidermodysplasia verruciformis, plane or intermediary skin warts), intra-epithelial neoplasias and cutaneous cancers, the cancers of the epidermodysplasia verruciformis, genital neoplasias, and cancers of the uterine cervix condylomas and papillomas.

The papillomaviruses are found associated with squamous intraepithelial lesions of the uterine cervix, known as cervical intraepithelial neoplasia (CIN), which may regress, remain stable, or progress into invasive squamous cell carcinomas (23, 31). It is likely that the variability of the clinical evolution of CIN reflects the diversity of the associated HPV types (3, 23).

Therefore, the identification of all genital HPV types is an important issue to understand fully the role of HPVs in the natural history of invasive carcinoma of the uterine cervix, which is the second most frequent cause of cancer-related mortality in women worldwide (31). Obviously, such knowledge would be of significant help to clinicians for the management of patients.

SUMMARY OF THE INVENTION

The present invention relates to the isolation and identification of papillomaviruses HPV68 and HPV70 and variants of these papillomaviruses.

The invention further relates to the genomic DNAs of HPV68 and HPV70 and fragments thereof. For example, some fragments relate to the genes of these HPVs including the genes encoding E1, E2, E6, E7, L1, L2, and the non coding intergenic region. Other fragments relate to the restriction enzyme sites as depicted in FIG. 2. Such fragments may be useful as primers or probes in the detection of the presence HPV68 or HPV70.

Moreover, immunogenic proteins of these viruses and expression vectors encoding these proteins are embodied by the invention. Such proteins include L1, L2, E6, and E7.

The invention also relates to products genetically or immunologically related to the HPV68 and HPV70 papillomaviruses.

BRIEF DESCRIPTION OF THE DRAWINGS

FIGS. 3(A) and (B) Nucleotide sequence alignments of the 3' end of the long control region, the E6 and E7 ORFs (A)(SEQ ID NOS 5–7, respectively), and the L1 ORF (B)(SEQ ID NOS 8–11, respectively) of HPV68 and 70 DNAs. The initiation and stop codons of the E6, E7, and L1 ORFs are underlined. The nucleotide sequence of ME180 HPV DNA (19) is given above the HPV68 sequence. Dots indicate identical nucleotides. Dashes represent spaces included for alignment purposes. The L1 sequence of the HPV70 NO87 isolate is represented beneath the HPV70 sequence, between the two BamHI sites underlined by a thick line. Substituted nucleotides in variants reported in the literature (Table 2) are indicated by lower case letters for HPV68 (above ME180 sequence) and HPV70 (beneath NO87 sequence) at positions 15, 16 81, 84, 99, 146, and 172 for the X02 isolate (11), 1245 for L1AE1, LVX160, and CP141 (16, 18, 25), 1283 and 1398 for CP141 (18). Variants were identified by sequencing a 211- or a 450-nucleotide fragment amplified by PCR, using L1C1 and L1C2 (11) or MY11 and MY09 (14) primers, respectively. The positions of primers are indicated by arrows. L1C1 ends four nucleotides upstream of the L1 ATG.

FIGS. 5(A)(SEQ ID NO:12) and (B)(SEQ ID NO:13) Nucleotide sequence of DNA of HPV 68.

FIG. 6(SEQ ID NO:12) Nucleotide sequence of DNA of HPV 70.

DESCRIPTION OF THE PREFERRED EMBODIMENTS

It is a common observation that Southern blot hybridization experiments performed in non stringent conditions (12, 21, 26) or PCR data obtained using consensus or degenerate primers (1, 4, 11, 14, 28) reveals the presence of HPV DNA sequences different from known HPV types in genital specimens. To be recognized as a novel HPV type, an HPV isolate should share less than 90% nucleotide sequence identity with known HPV types in the E6, E7, and L1 open reading frames (ORFs) and its entire genome should be cloned (7, 17). We report here the characterization of two novel genital HPV types, HPV68 and HPV70, related to the potentially oncogenic HPV 39 (2).

Therefore, this invention relates to the genomic DNAs of HPV68 and HPV70 and particularly, to purified DNA of HPV68 and HPV70. More particularly, the HPV-DNAs of the claimed invention have the restriction sites set forth in FIG. 2. In addition, the invention further relates to HPV-DNAs having the nucleotide sequences shown in FIGS. 5 and 6.

The invention also relates to fragments of each of the preceding DNA-HPVs or to DNA-HPVs capable of hybridizing with them and particularly, under stringent conditions. Similarly, it relates to recombinant DNAs containing all or part of the DNA-HPVs mentioned above, and more particularly to the recombinant DNAs containing fragments corresponding to the genes E1, E2, E6, E7, L1, L2, and the non coding intergenic region.

Figure 2:
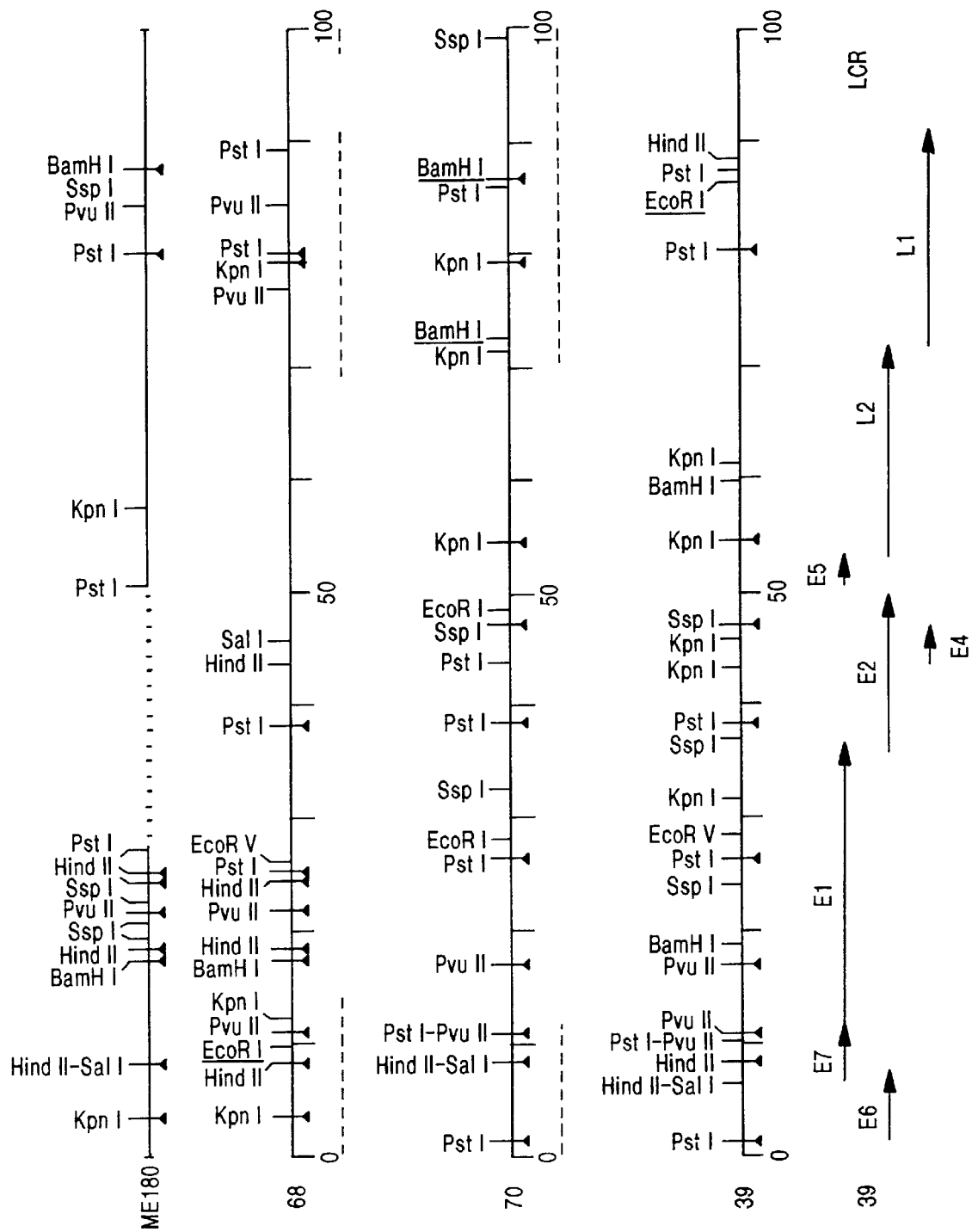
FIG. 2 Physical maps of HPV68 and 70 DNAs and their alignment with the maps of HPV39 and ME180 sequences. The cloning restriction sites are underlined. Cleavage sites conserved between at least two genomes are indicated by arrowheads. Dashes underline sequenced regions of HPV68 and 70 DNAs. The missing sequences of ME180 DNA (19) are noted by a dashed line. The genetic map of HPV39 (30) is represented at the bottom of the figure. The enzymes AvaI, BglII, ClaI, Hind II, SacI, SmaI, SspI, ZbaI, and ZhoI have no cleavage sites in HPV68 DNA. The enzymes AvaI, BglI, BglII, EcoRV, HpaI, PvuI, SacII, SmaI, XbaI, and XhoI have no cleavage sites in HPV70 DNA.

Additional HPV DNA fragments of the claimed invention relate to the restriction enzyme sites as depicted in FIG. 2. In particular, the restriction sites of the HPV68 DNA include those fragments corresponding to KpnI, HindII, EcoRI, PvuII, KpnI, BamHI, PstI, EcoRV, and SalI, for example. Moreover, the restriction sites of the HPV70 DNA include those fragments corresponding to PstI, HindII-SalI, PstI-PvuII, PvuII, EcoRI, SspI, KpnI, and BamHI, for example.

It also relates to probes that may be constituted from these DNA-HPVs or from corresponding fragments. Probes of the claimed invention are selected and synthesized according to methods well-known in the art. These probes may be selected and synthesized by methods known in the art at the time this claimed invention was made. In addition, these probes or mixtures containing them may be useful in in vitro diagnostic procedures for the detection of an infection by the papillomavirus or a variant of the papillomavirus. Preferably, these probes may further be labeled with a radioactive marker or a non-radioactive marker.

The process for the in vitro diagnosis in a biological sample to be tested for the presence of a papillomavirus (HPV68 or HPV70) or by a variant thereof using a labeled probe of the claimed invention involves contacting the labeled probe with nucleic acids of the sample under stringent hybridization conditions and detecting a hybrid formed between the nucleic acids present in the biological sample and the probe. The detection of the hybrid is correlated with the presence of the papillomavirus.

It is further to be understood that the probes of the claimed invention can be further used in combination with probes derived from other papillomaviruses.

The invention also relates to the use of the peptides as primers in PCR methods, as known in the art, for the detection of an infection of HPV68 or HPV70.

The invention also relates to use of the DNA and encoded proteins for immunization purposes. The use of isolated polynucleotides to provide an immune response upon in vivo translation of the polynucleotide is described, for example, in WO 90/11092, published Oct. 4, 1990 (Felgner, P., et al.), which is incorporated herein by reference.

In particular, the invention relates to expression products or polypeptides encoded by fragments of HPV68 DNA or HPV70 DNA according to the claimed invention. Such polypeptides include L1, L2, E1, E2, E6, and E7 and may be useful as antigens. These polypeptides are synthesized by methods known in the art and are preferably in purified form.

It should be noted that the expression products or polypeptides of the claimed invention embody various products derived from its original DNA whether it corresponds to RNAs or recombinant DNAs containing all or part of the original DNA as well as the "immunological" products resulting from the expression of these DNAs or recombinant DNAs in competent cell hosts. Thus, they are polypeptides resulting from the transcription and translation of all or part of the different open reading frames of the original DNA.

The purified polypeptides of the invention may be useful for the production and purification of antibodies found in the sera of a patient having HPV68 or HPV70. In particular, animals are immunized with these antigens and antibodies against these antigens are produced by the immunized animal. The antibodies are further purified by known methods in the art, for example, by passing the serum of the animal containing the antibodies through affinity columns bearing the above-mentioned polypeptides. The antibodies selectively bound to these columns can then be recovered by dissociation of the antigen-antibody complexes by means of a suitable buffer possessing an adequate ionic strength, for example, a solution of a salt such as ammonium acetate.

The invention further relates to the production of antibodies to the above-mentioned polypeptides. Preferably, the expression products of the genes L1, L2, E1, E2, E6, and E7, of each of the papillomaviruses according to the invention are used to produce the antibodies of the claimed invention. The process for the production of antibodies involves immunizing a suitable living host with the expression products of the invention, and recovering the antibodies formed from the serum of the immunized host by methods known in the art. In particular, this comprises placing the sera in contact with the corresponding polypeptides in the purified state, and recovering the antibodies from the antigen-antibody complexes formed.

The invention further relates to the method of detecting an infection due to HPV68 or HPV70 using the antibodies produced according to the invention. The method comprises placing the antibody with the biological sample and detecting the antigen-antibody complex. The detection of the complex is correlated with the presence of an infection due to HPV68 or HPV70.

Finally, the invention relates to a process for producing cloned recombinant human papillomavirus DNA comprising the step of cloning a vector in a host cell, wherein the vector comprises the genomic DNA or fragment thereof of HPV68 or HPV70. Preferably, the DNA is selected from the group consisting of genomic DNA and DNA fragments encoding a protein selected from the group consisting L1, L2, E1, E2, E6, and E7.

The preparations of the viral DNAs were extracted according to the techniques described below.

In what follows, the conditions under which each of the papillomaviruses according to the invention was isolated are described, and the conditions under which the DNA-HPV was obtained from the particular papillomavirus, are described.

EXAMPLE 1

Cloning and restriction maps of HPV68 and 70 genomes

HPV68 was cloned from a biopsy of a low grade CIN. HPV-related DNA sequences were detected by Southern blot hybridization of the PstI-digested total DNA preparation with mixtures of [$^{32}$p]-labeled HPV6, 11 and 42, HPV16, 18 and 33, or HPV31, 35 and 39 DNA probes. The signal was strongest with the mixture of HPV31, 35, and 39 probes, whether under non stringent conditions of hybridization (Tm-40° C.) or after washing under more stringent conditions in which signals were reduced (Tm-20° C.).

The full-length HPV genome was cloned after insertion into the bacteriophage lambda ZAP II DNA at the EcoRI site and subsequently subcloned into the Bluescript II phagemid (Stratagene, La Jolla, Calif.). Hybridization of the original DNA preparation with the cloned DNA as a probe revealed a 7.9 kb fragment after cleavage with BanHI or EcoRI endonucleases and from four to six DNA fragments after digestion with AvaII, BanI, or PstI (FIG. IA).

Cross-hybridization experiments performed under stringent conditions (Tm-10° C.) between the [$^{32}$p]-labeled cloned HPV DNA and the DNA of known cutaneous and genital HPV types showed a strong hybridization with HPV39 and a weak hybridization with HPV18, 45, and 59. A physical map was constructed from the study of DNA cleavage patterns obtained with 17 restriction endonucleases (FIG. 2). Partial nucleotide sequence data (see below) confirmed the localization of the involved restriction sites and allowed the map to be aligned with that of the HPV 39 genome (30).

HPV70 was cloned from a biopsy of a vulvar papilloma from an immunosuppressed renal allograft recipient. In a first attempt, a cloned 6.8-kb BamHI fragment showed a 16% cross-hybridization with HPV39 DNA as evaluated by liquid phase hybridization experiments suggesting that this isolate represented a novel HPV type (2). Heteroduplex analysis had allowed the alignment of the restriction maps of the HPV39 genome and the 6.8-kb fragment and had shown that the missing sequences corresponded to the ORF L1 (2). Due to the very small amount of DNA available, direct cloning of the lacking BamHI fragment was not possible. We thus amplified the missing sequences by a nested PCR method. To design the primers, the region flanking the BamHI sites within the 6–8-kb fragment was sequenced by the dideoxy chain terminator method (22). The primers used for the first step of PCR were located 280 nucleotides upstream of the 5' BamHI site (SEQ ID NO:1) (5'-GGCGAAGGTTGTCAATACAG-3') and 360 nucleotides downstream of the 3' BamHI site (SEQ ID NO:2)(5'-ACCAGGACAAACATATACAG-3').

Amplification was performed with an automated thermal cycler (Hybaid, United Kingdom), in 100 μl reaction mixtures containing 10 mM Tris-HCl, pH 8.3, 50 mM KCl, 1.5 mM MgCl$_2$, 250 μM of each deoxynucleoside triphosphate, 30 pmol of each primer, 1.25 U Taq polymerase (AmpliTaq DNA Polymerase, Perkin-Elmer Cetus, Norwalk, Conn.) and 1 μg of the biopsy DNA. After an initial denaturation at 94° C. for 5 min, each of the 20 cycles consisted of a 1 min denaturation step at 95° C., 2 min primer annealing at 55° C., and 2 min chain extension at 72° C. The extension of all amplified products was completed by a final extension step of 3 min at 72° C. A second amplification was performed on the PCR products (2 μl) under the same conditions, using primers located 71 nucleotides upstream of the 5' BamHI site (SEQ ID NO:3)(5$^1$-CCTAAGGTGTCTGCATATCA-3') and 66 nucleotides downstream of the 3' BamHI site (SEQ ID NO:6)(5'-AACTGATCTAGTTCTGTACT-3').

The 1.1.kb BamHI fragment obtained after enzymatic digestion of the PCR products was cloned into Bluescript II phagemid. Sequencing of three independent recombinant plasmids yielded the same nucleotide sequence, rendering unlikely the introduction of nucleotide substitutions by the Taq DNA polymerase. These sequence data and those on E6 and E7 ORFs (see below) were used, together with the restriction map of the 6.8-kb fragment (2), to establish a physical map of HPV70 and to align it with the maps of HPV39 and 68 DNAs (FIG. 2).

Figure 1A:
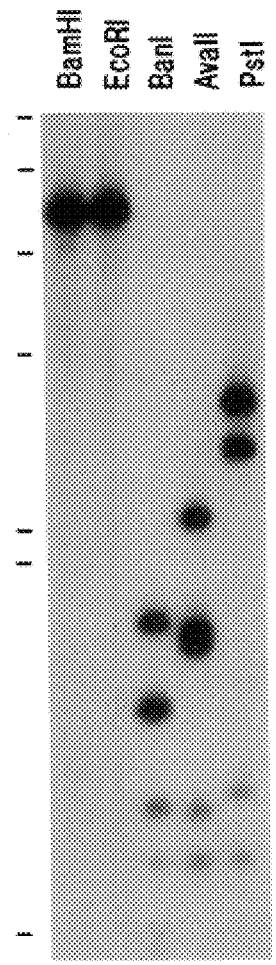
FIG. 1(A) Blot hybridization analysis of HPV68 DNA sequences found in a CIN I. The total cellular DNA extracted from the biopsy (1.5 µg) was cleaved with different endonucleases, as indicated. The fragments were separated by electrophoresis in an 1% agarose gel, denatured in situ, and transferred to a nylon membrane (Amersham, U.K.). The membrane was hybridized under stringent conditions (Tm-10° C.), by using a [$^{32}$p]-labeled HPV68 DNA probe. The migration of λ DNA Hind III fragments is indicated on the left. (B). DNA sequence homology among HPV 39, 68, and 70, as analyzed by blot hybridization. Cloned HPV DNAs were excised from plasmid sequences by digestion with BamHI (HPV70) or EcoRI (HPV39 and 68) endonucleases, purified and cleaved with PstI endonuclease. Blot hybridization experiments were performed in stringent conditions (Tm-10° C.), using HPV68, HPV70, or HPV39 DNA probes, as indicated. The open reading frames contained in the HPV DNA fragments corresponding to each probe (see FIG. 2) are indicated on the left.
Figure 1B:
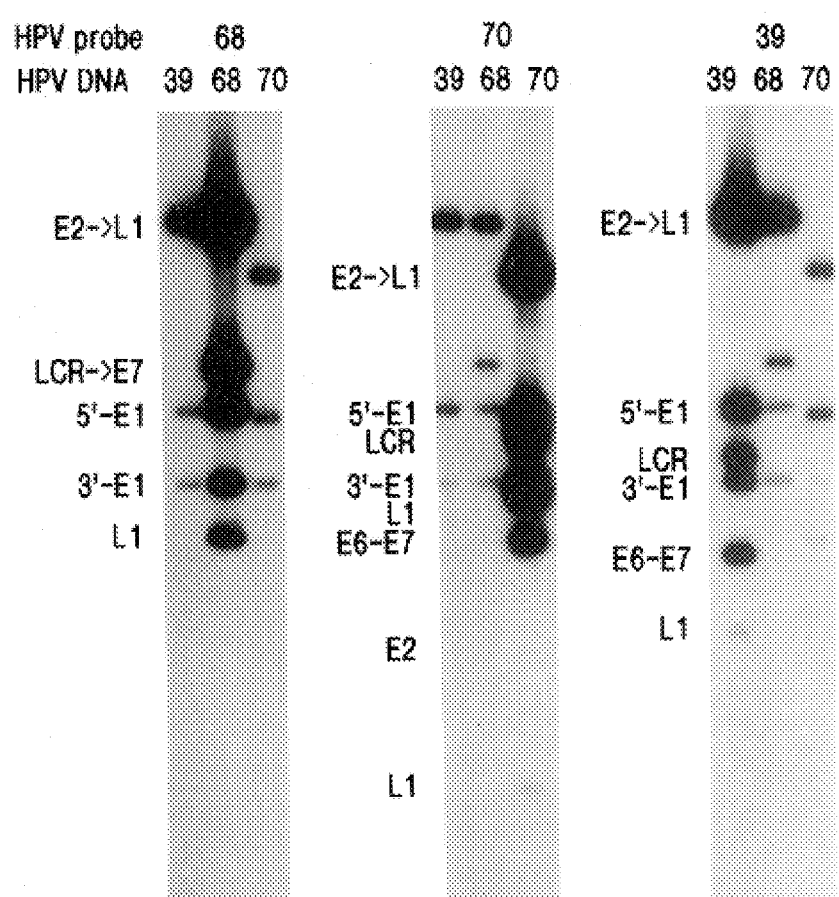

Of the 19 cleavage sites mapped on the HPV68 genome, 4 sites were found conserved in HPV39 and 70 DNAs, one in HPV39 and one in HPV70. Among the 20 restriction sites mapped on the HPV70 genome 4 additional sites were found to be shared with HPV39 DNA (FIG. 2). The relationship between HPV39, 68, and 70 DNAs was further shown by cross-hybridization experiments performed under stringent conditions (Tm-10° C.), using the excised cloned HPV39, 68, and 70 DNAs digested with PstI endonuclease (FIG. 1B). Most of the DNA fragments were detected with heterologous probes, even if displaying much weaker signals than with homologous probes. As anticipated from the presence of conserved PstI sites, fragments with the same sizes were common to two or three of the HPV types, namely, the larger HPV39 and HPV68 PstI fragment encompassing E2, L2, and L1 ORFs and the HPV39, 68, and 70 PstI fragment containing the 3' end of E1 (FIG. 1B).

EXAMPLE 2

Comparison of the nucleotide sequence of the E6, E7 and L1 ORFs of HPV39. 68. and 70

To determine the nucleotide sequence of the E6, E7, and L1 ORFs (FIGS. 3A–B), appropriate restriction fragments of HPV68 and HPV70 DNAs subcloned in pBluescript II were sequenced. Sequence determination was performed in both orientations by the dideoxy method (22), first using universal primers (Stratagene), and then, synthetic oligonucleotides (Genset, Paris, France) chosen from newly established sequences. On the whole, 3,168 nucleotides were sequenced for HPV68, encompassing the 3' end of L2 ORF, the L1 ORF, the 5' and 3' ends of the long control region (LCR), the E6 and E7 ORFs, and the 5' end of E1 ORF (FIG. 2). A 3,283 nucleotide segment, from the 3' end of the L2 ORF to the 5' end of the E1 ORF, was sequenced for the HPV70 genome (FIG. 2). Sequence comparison was done with the Sequence Analysis Software Package (Genetics Computer Group Inc., Madison, Wis.).

Pairwise alignment of HPV39 (30), 68, and 70 sequences, performed using the FASTA program, disclosed 82% nucleotide identity between HPV68 and HPV39, 79% between HPV39 and HPV70, and 81% between HPV68 and HPV70. The percentage of identical nucleotides in E6, E7, and L1 ORFs varies between 81% and 89% (FIGS. 3A,B, Table 1). This warrants the recognition of 3 distinct HPV types.

TABLE 1

Percentage of identity of nucleotide and deduced amino acid sequences

| Compared HPV sequences | Nucleotide sequence | | | | Amino acid sequence | | |
|---|---|---|---|---|---|---|---|
| | 3'-LCR | E6 | E7 | L1 | E6 | E7 | L1 |
| HPV68 vs HPV39 | 72 | 87 | 89 | 81 | 85 | 83 | 87 |
| HPV68 vs ME180 | 86 | 94 | 95 | 93 | 93 | 89 | 95 |
| HPV70 vs HPV39 | 71 | 87 | 86 | 81 | 82 | 76 | 86 |
| HPV68 vs HPV70 | 68 | 85 | 85 | 81 | 82 | 76 | 86 |
| HPV68 vs HPV18 | 54 | 70 | 72 | 75 | 63 | 61 | 75 |
| HPV70 vs HPV18 | 55 | 72 | 75 | 75 | 66 | 64 | 76 |

The percentage of identity of the deduced amino acid sequences varies between 76% and 87%. The three E6 proteins have the same size (158 amino acids), whereas the size of the E7 proteins (109 amino acids for HPV39 and 70, 110 for HPV68) and L1 proteins (505 amino acids for HPV39 and 68, 506 for HPV70) differ by one amino acid.

The 3' end of the LCR (about 300 nucleotides) shows a higher nucleotide sequence variation (FIG. 3A, Table 1). Furthermore, the LCR of HPV70 (see accession number below) is 114-nucleotides longer than that of HPV39 (30), due to insertions/deletions in the 5' region. When compared to HPV18 (6), a highly oncogenic related type, HPV39, HPV68, and HPV70 showed a percentage of identical nucleotides in E6, E7, and L1 ORFs varying from 70 to 75%, with identical amino acids ranging from 61% to 76% (Table 1).

Figure 3B-1:
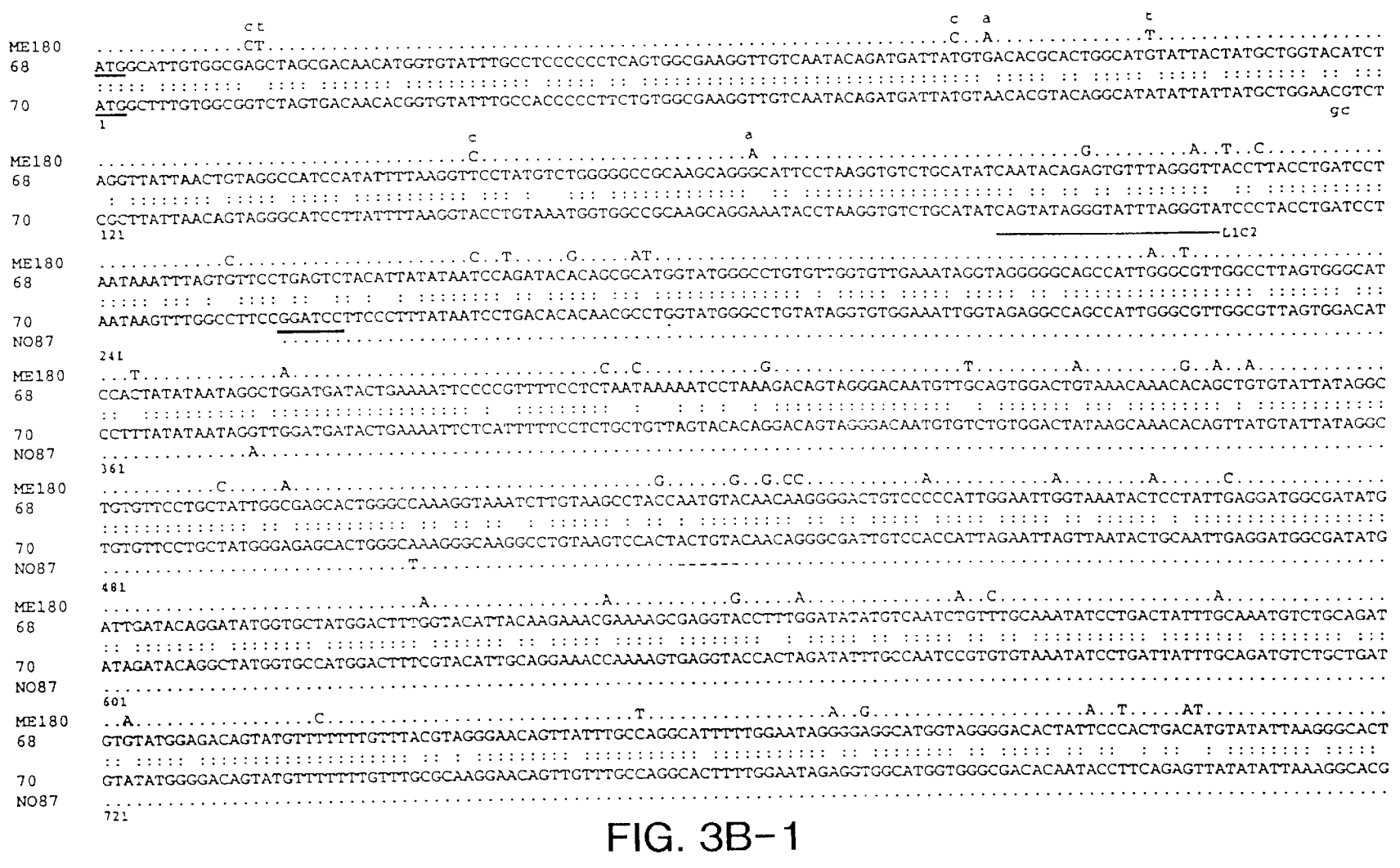

The ME180-HPV DNA sequence, a 5,993 bp fragment cloned from the cervical carcinoma-derived ME 180 cell line, has been reported to be related to HPV39 (19). The unavailability of the complete genome precluded its recognition as a new HPV type (19). When compared, HPV68 and ME 180 nucleotide sequences show 93% identity for the 3,168 nucleotides analyzed and 93% to 94% identity in the E6, E7, and L1 ORFs (FIGS. 3A–B, Table 1). Amino acid sequence identity varies from 89% to 95% for the encoded proteins (Table 1). HPV subtypes are defined by a nucleotide sequence variability of 2 to 10% in the E6, E7, and L1 ORFs, whereas variants show a sequence variability lesser than 2% (4, 5, 7, 8). The prototypical HPV68 and ME 180 HPV DNA sequence may thus be considered as two subtypes, HPV68a and HPV68b, respectively. It is worth stressing that when restriction maps for 9 endonucleases are compared (FIG. 2), only 8 of the 16 HPV68 sites and the 18 HPV ME180 sites were found conserved.

Figure 4:
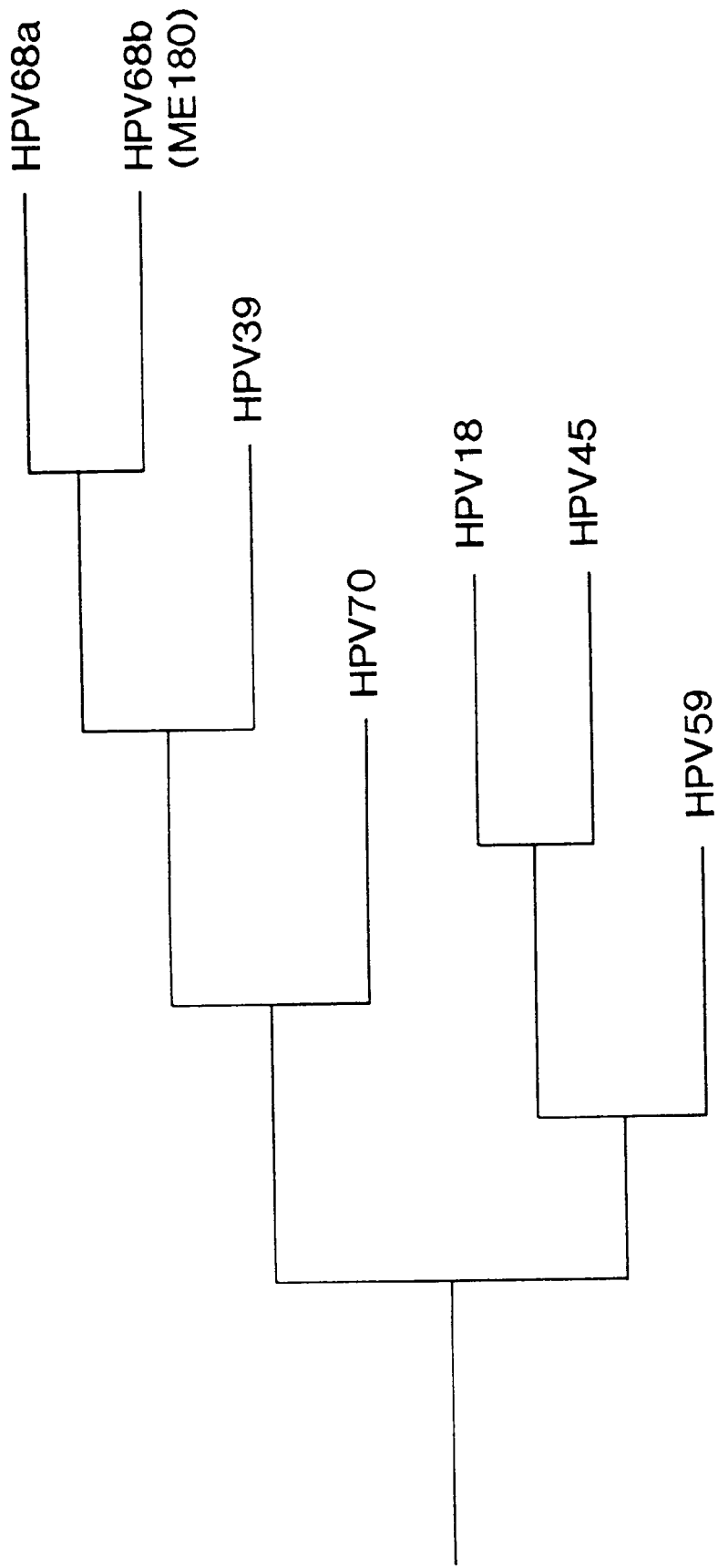
FIG. 4 Phylogenetic relationships among HPV18-related types. A tree was constructed from the comparison of aligned E6 proteins using maximum parsimony algorithms in the PHYLIP 3.5 package (24). The tree was rooted using HRV51.

To evaluate the evolutionary relationships between HPV68, 70, 39, and ME180 and the related HPV types 18, 45, and 59 (6, 15, 20), the deduced amino acid sequences of the E6 and L1 ORFs were aligned, using the Clustal W program (9, 27), and phylogenetic trees were generated, using the Phylogenetic Inference Package (PHYLIP 3.5.) (24). The trees were rooted taking HPV51 (13) as an outgroup. The same trees were obtained by both maximum sequence parsimony analysis and distance matrix analysis. Bootstrap resampling (100 replicates) indicates a 91.5%–94.1 confidence level for the grouping of HPV39, 68, and 70. As illustrated for E6 amino acid sequences (FIG. 4). HPV68 appears more related to HPV39 than to HPV70. All three viruses, together with HPV types 18, 45 and 59, constitute one of the branches of the subgroup containing HPV types associated with high grade CIN and invasive cancer (29).

EXAMPLE 3

Prevalence variability and pathogenicity of HPV68 and 70

In the course of the screening of about 3,000 genital samples for the presence of HPV DNA sequences, HPV39-related sequences were detected in specimens of six patients by Southern blot hybridization. HPV68 was found in four specimens, the low grade CIN from which the prototype was cloned, a low grade CIN from an HIV seropositive patient, a low grade intraepithelial neoplasia of the vagina from a renal allograft recipient, and a penile Bowenoid papule. All four HPV68 isolates showed the PstI cleavage pattern illustrated in FIG. 1A. HPV70 was detected in the two other specimens, the vulvar papilloma from which the prototype was cloned and a low grade CIN. The HPV70 isolate from this lesion, referred to as NO87, showed a distinct PstI cleavage pattern.

Figure 3B-2:
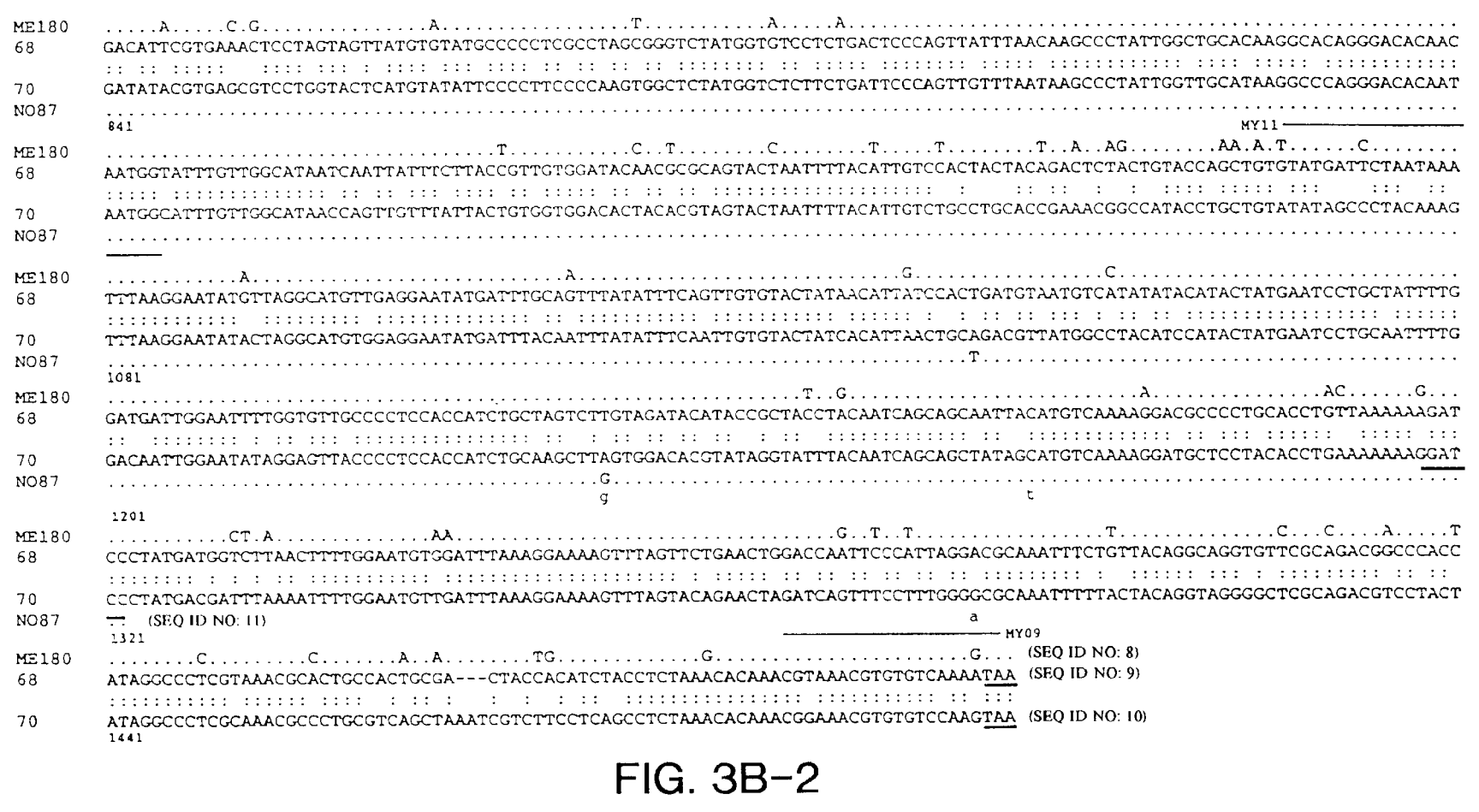

To characterize the L1 region of NO87 isolate, the 1.1-kb BamHI fragment was amplified by the PCR method and cloned, as described above for the prototypical HPV70. When compared to the prototypical nucleotide sequence, this fragment (1059 bp) showed four silent nucleotide substitutions and a 6-nucleotide deletion affecting codons 179 and 180 (FIG. 3, Table 2). One of the four nucleotide substitutions involved a PstI site. Since the two isolates differ by less than 1% in the L1 region, it is likely that they represent variants.

TABLE 2

Evidence for additional HPV68 and 70 isolates from published L1 ORF nucleotide (nt) sequence data

| HPV Isolates (reference) | Origin | Diagnosis | Variable vs. total nts[b] | Amino acid changes[b] |
| --- | --- | --- | --- | --- |
| HPV68 | | | | |
| ME180(19) | USA | SCC | 110/1518 | 27 amino acids |
| X02(11) | Japan | CIN III | 7/204 | Ala-6 –> Ser |
| | | | 0/204[c] | none |
| 1111(10) | Zaire | CIN | 3/335[c] | none |
| HPV70 | | | | |
| NO87 (this study) | France | CIN I | 10/1064 | del Thr-179 Val-180 |
| X11(11) | Japan | SCC | 2/204 | Thr-39 –> Ser |
| L1AE1(25) | USA | Normal | 1/454 | none |
| LVX160(16) | Brazil Singapore | Unknown Unknown | 1/454 | none |
| CP141(18) | USA | Normal | 3/454 | Ala-428 –> Val |

[a]SCC, invasive cervical squamous cell carcinoma. CIN1 or III, cervical intraepithelial neoplasia grade I or III.
[b]As compared to the prototypes described in this study. Variable nucleotides are detailed in FIG. 3.
[c]As compared to ME180 isolate.

Two HPV types related to HPV 39, a potentially oncogenic genital virus (2, 30), have been characterized. As compared to HPV39, found in about 3.5% of HPV-positive cervical specimens (1, 3, S. Beaudenon, P. Cassonnet, R. Barrasso and G. Orth, unpublished results), HPV68 and HPV70 have been seldom detected in our screening series and three of the six positive specimens originated from immunosuppressed patients. In spite of this low prevalence, sequence data on DNA fragments of the L1 region obtained by PCR amplification, using consensus or degenerate primers, indicate the occurrence of HPV68 and HPV70 worldwide (10, 11, 16, 18, 19, 25) (Table 2). Two HPV68 isolates, X02 (11) and 1111 (10), are identical or closely related to ME180-HPV (19) (FIG. 3B, Table 2). The substantial differences observed between ME180 and the prototypical HPV68 (7% nucleotide divergence) are thus unlikely to result from the long-term maintenance of the ME180 cell line in tissue culture, but rather support the existence of two subtypes, HPV68a and HPV68b (ME180 HPV).

Similarly, five isolates identified by others (11, 16, 18, 25) are closely related to HPV70 (FIG. 3B, Table 2). All isolates show a nucleotide sequence variability of less than 1% when compared to the prototype described herein. Three isolates identified in distinct parts of the world, LVX160 found twice (16) and L1AE1 (25), show the same nucleotide sequence and differ from the prototype by one out of the 454 nucleotides sequenced. Furthermore, a Swedish isolate was found to be identical to the French NO87 variant for the 1059 nucleotides compared, both isolates displaying the same deletion of two adjacent codons (Thr-179, Val-180) in the L1 protein (0. Forslund and B. G. Hansson, unpublished results). These data point to the stability of HPV70 variants and indicate that the genetic variability in the coding regions of HPVs involves not only point mutations, but also insertion/deletion events.

Two of the HPV68 and HPV70 isolates identified so far, ME180 and X11, have been isolated from invasive cervical carcinomas (11, 19), and three are from CIN lesions (10, 11) (Table 2). Moreover, these isolates have been identified in Europe, Africa, North and South America, and Asia (Table 2). Thus, HPV68 and HPV70 should be considered as worldwide distributed, potentially oncogenic, HPV39-related genital HPV types.

The invention also relates to any recombinant DNA containing HPV 68 and/or HPV 70 DNA, or fragments thereof, for hybridization probes, as described in U.S. Pat. No. 5,342,930, which is incorporated herein by reference. The invention further relates to cell cultures transformed with this recombinant DNA, products of expression of the DNA, corresponding antibodies produced against these expression products, and methods of using these expression products and antibodies, also as described in U.S. Pat. No. 5,342,930.

Nucleotide accession numbers. The nucleotide sequence accession numbers X67160, X67161, and U22461 were assigned to HPV68 and HPV70.

HPV 68 DNA was deposited with the National Collection of Cultures of Microorganisms (C.N.C.M.), Institut Pasteur, 28 rue du Docteur Roux, 75724 Paris Cedex 15, France, on Feb. 16, 1995, under Accession Number I-1540.

HPV 70 DNA was deposited with the National Collection of Cultures of Microorganisms (C.N.C.M.), Institut Pasteur, 28 rue du Docteur Roux, 75724 Paris Cedex 15, France, on Feb. 15, 1996, under Accession Number I-1674 (PVH70 BamH1 1.1 kb) and Accession Number I-1675 (PVH70 BamH1 6.8 kb).

REFERENCES

1. Bauer, H. M., V. Ting, C. E. Greer, J. C. Chambers, C. J. Tashiro, J. Chlmera, A. Reingold, and M. Manos. 1991. Genital human papillomavirus infection in female university students as determined by a PCR-based method. JAMA. 265:472–477.
2. Beaudenon, S., D. Kremsdorf, S. Obalek, S. Jablonska, G. Pehau-Arnaudet, O. Croissant, and G. Orth. 1987. Plurality of genital human papillomaviruses: characterization of two new types with distinct biological properties. Virology. 161:374–384.
3. Bergeron, C., R. Barrasso, S. Beaudenon, P. Flamant, O. Croissant, and G. Orth. 1992. Human papillomaviruses associated with cervical intraepithelial neoplasia: Great diversity and distinct distribution in low-and high-grade lesions. Am. J. Surg. Pathol. 16:641–649.
4. Bernard, H. -U., S. -Y. Chan, M. M. Manos, C. -K. Ong, L. L. Villa, H. Delius, C. L. Peyton, H. M. Bauer, and C. M. Wheeler, 1994. Identification and assessment of known and novel human papillomaviruses by polymerase chain reaction amplification, restriction fragment length polymorphisms, nucleotide sequence, and phylogenetic algorithms J. Infect. Dis. 170:1077–1085.
5. Chan, S. -Y., H. -U. Bernard, C. -K. Ong, S. -P. Chan, B. Hofman, and H. Delius. 1992. Phylogenetic analysis of 48 papillomavirus types and 28 subtypes and variants; a showcase for the molecular evolution of DNA viruses. J. Virol. 66:5714–5725.
6. Cole, S. T., and O. Danos. 1987. Nucleotide sequence and comparative analysis of the human papillomavirus type 18 genome; Phylogeny of papillomaviruses and repeated structure of the E6 and E7 gene products. J. Mol. Biol. 193:599–608.
7. de Villiers, E. -M. 1994. Human pathogenic papillomavirus types. Curr. Top. Microbiol. Immunol. 186:1–12.
8. Deau, M. -C., M. Favre, 5. Jablonska, L. -A. Rueda, and G. Orth. 1993. Genetic heterogeneity of oncogenic human papillomavirus type 5 (HPV5) and phylogeny of HPV5 variants associated with epidermodysplasia verruciformis. J. Clin. Microbiol. 31;2918–2926.
9. Higgins, D. G., A. J. Bleasby, and R. Fuchs. 1992. CLUSTAL V: improved software for multiple sequence alignment. CABIOS. 8:189–191.
10. Icenogle, J. P., M. Laga, D. Miller, A. T. Manoka, R. A. Tucker, and W. C. Reeves. 1992. Genotypes and sequence variants of human papillomavirus DNAs from human immunodeficiency virus type 1-infected women with cervical intraepithelial neoplasia. J. Infect. Dis. 166:1210–1216.
11. Iwamoto, A., H. Yoshikawa, K. Kitagawa, H. lgarashi, T. Kawana, and H. Yoshikura. 1992. Short sequence in L1 region of human papillomaviruses correlates with clinical pictures and grouping by cross-hybridization. Jpn. J. Cancer Res. 83:315–319.
12. Lörincz, A. T., R. Reid, A. B. Jenson, M. D. Greenberg, W. Lancaster, and R. J. Kurman. 1992. Human papillomavirus infection of the cervix; relative risk associations of 15 common anogenital types. Obstet. Gynecol. 79:328.337.
13. Lungu, O., C. R. Crum, and S. Silverstein. 1991. Biologic properties and nucleotide sequence analysis of human papillomavirus type 51. J. Virol. 65:4216–4225.
14. Manos, M. M., Y. Ting, D. K. Wright, A. J. Lewis, T. R. Broker, and S. R. Wolinsky. 1989. The use of the polymerase chain reaction amplification for the detection of genital human papillomaviruses. Cancer Cells. 7:209–214.
15. Naghashfar, Z. S., N. B. Rosenshein, A. T. Lorincz, J. Buscema, and K. V. Shah. 1987. Characterization of human papillomavirus type 45, a new type 18-related virus of the genital tract. J. Gen. Virol. 68:3073–3079.
16. Ong, C. -K., H. -U. Bernard, and L. L. Villa. 1994. Identification of genomic sequences of three novel human papillomavirus sequences in cervical smears of Amazonian indians. J. Infect. Dis. 170:1086–1088.
17. Orth, G. 1994. Human papillomaviruses: general features, p. 1013–1021. In R. G. Webster and A. Granhoff (ed.), Encyclopedia of Virology vol. 2. Academic Press Ltd., London.
18. Peyton, C L., and C. M. Wheeler. 1994. Identification of five novel human papillomavirus sequences in the New Mexico triethnic population. J Infect Dis. 170:1089–1092.
19. Reuter, S., H. Delius, T. Kahn, Hofmann, H. zur Hausen, and E. Schwarz. 1991. Characterization of a novel human papillomavirus DNA in the cervical carcinoma cell line ME180. J. Virol. 65:5564–5568.
20. Rho, J., A. Roy-Burman, H. Kim, E. -M. de Villiers, T. Matsukura, and J. Choe. 1994. Nucleotide sequence and phylogenetic classification of human papillomavirus type 59. Virology. 203:158–161.
21. Riou, G., M. Favre, D. Jeannel, J. Bourhis, V. Le Doussal, and G. Orth. 1990. Association between poor prognosis in early-stage invasive cervical carcinomas and non detection of HPV DNA. Lancet. 335:1171–1174.
22. Sanger, F., S Nicklen, and A. R. Coulson. 1977. DNA sequencing with chain-terminating inhibitors. Proc. Natl. Acad. Sci. USA. 74:5463–5487.
23. Schiffman, M. H., H. M. Bauer, R. N. Hoover, A. O. Glass, D. M. Cadell, B. B. Rush, D. R. Scott, M. E. Sherman, R. J. Kurman, S. Wacholder, C. K. Stanton, and M. M. Manos. 1993. Epidemiologic evidence showing that human papillomavirus infection causes most cervical intraepithelial neoplasia. J. Nat. Cancer Inst. 85:958–964.

24. Swofford, D. L. 1991. PAUP: Phylogenetic Analysis Using Parsimony (version 3.1.), Computer Program distributed by Illinois Natural History Survey, Champaign, Ill.
25. Tachezy, R., M. A. van Ranst, Y. Cruz, and R. D. Burk. 1994. Analysis of short novel human papillomavirus sequences. Biochem Biophys. Res. Commun. 204:820–827.
26. Tawheed, A. R., S. Beaudenon, M. Favre, and G. Orth. 1991. Characterization of human papillomavirus type 66 from an invasive carcinoma of the uterine cervix. J. Clin. Microbiol. 29:2656–2660.
27. Thompson, J. D., D. G. Higgins, and T. J. Gibson. 1994. CLUSTAL W; improving the sensitivity of progressive multiple sequence alignment through sequence weighting, position-specific gap prenalties and weight matrix choice. Nucleic Acids Res. 22:4673–4680.
28. van den Brule, A. J. C., P. J. F. Snijders, P. M. C. Raaphorst, H. F. J. Schrijnemakers, H. Delius, L. Gissmann, C. J. L. M. Meijer, and J. M. M. Walboomers. 1992. General primer polymerase chain reaction in combination with sequence analysis for identification of potentially novel human papillomavirus genotypes in cervical lesions. J. Clin. Microbiol. 30:1716–1721.
29. Van Ranst, M., J. B. Kaplan, and R. D. Burk. 1992. Phylogenetic classification of human papillomaviruses: correlation with clinical manifestations. J. Gen. Virol. 73:2653–2660.
30. Volpers, C., and R. E. Streeck. 1991. Genome organization and nucleotide sequence of human papillomavirus type 39. Virology. 181:419–423.
31. zur Hauzen, H. 1991. Human papillomaviruses in the pathogenesis of anogenital cancer. Virology. 184:9–13.

What is claimed is:

1. Purified human papillomavirus (HPV) 68 DNA deposited at C.N.C.M. (Collection Nationale de Culture de Microorganisms) under Accession No. I-1540.

2. Purified human papillomavirus (HPV) 68 DNA sequence, which is selected from the group consisting of SEQ ID NO:12 and SEQ ID NO:13.

3. A purified HPV-68a nucleotide sequence encoding a protein, wherein said protein is selected from the group consisting of L1, L2, E6, and E7.

4. A purified HPV-68a nucleotide sequence according to claim 3, wherein said purified HPV-68a sequence, as set forth in FIG. 3A (SEQ ID NO:6), encodes the E6 protein.

5. A purified HPV-68a nucleotide sequence according to claim 3, wherein said purified HPV-68a sequence, as set forth in FIG. 3A (SEQ ID NO:6), encodes the E7 protein.

6. A purified HPV-68a nucleotide sequence according to claim 3, wherein said purified HPV-68a sequence, as set forth in FIG. 3B (SEQ ID NO:9), encodes the L1 protein.

7. The nucleotide sequence of claim 3, wherein said nucleotide sequence is labeled.

8. The nucleotide sequence of claim 7, wherein said label is selected from the group consisting of a radioactive marker and a nonradioactive marker.

9. A method of detecting HPV 68 in a biological sample containing nucleic acids, said method comprising contacting the nucleic acids of said biological sample with the HPV 68 DNA of either claim 1 or 2, wherein said DNA is labeled with a label selected from the group consisting of a radioactive marker and a non-radioactive marker;

detecting a hybrid between said HPV 68 DNA and said nucleic acids in the sample; and correlating the presence of said hybrid with the presence of HPV 68 in said sample.

10. A method of detecting HPV 68 in a biological sample containing nucleic acids, said method comprising contacting the nucleic acids of said biological sample with the nucleotide sequence of claim 7;

detecting a hybrid between said nucleotide sequence and said nucleic acids in the sample; and correlating the presence of said hybrid with the presence of HPV 68 in said sample.

11. A process for producing cloned recombinant human papillomavirus DNA, wherein the process comprises cloning a vector in a host cell, wherein said vector comprises a human papillomavirus 68 DNA deposited at C.N.C.M. (Collection Nationale de Culture de Microorganisms) Under Accession No. I-1540.

12. The process of claim 11, wherein said vector comprises a purified human papillomavirus HPV-68a DNA sequence wherein the sequence is selected from the group consisting of SEQ ID NO: 12, and SEQ ID NO: 13.

13. The process of claim 11, wherein said vector comprises a purified human papillomavirus HPV-68a nucleotide sequence encoding a protein, wherein said protein is selected from the group consisting of L1, L2, E6, and E7.

* * * * *

UNITED STATES PATENT AND TRADEMARK OFFICE
CERTIFICATE OF CORRECTION

PATENT NO. : 5,981,173
DATED : November 9, 1999
INVENTOR(S) : Gerard Orth, et al.

It is certified that error appears in the above-identified patent and that said Letters Patent is hereby corrected as shown below:

On the Title Page:

Item: [73] line 2, under "Assignees", delete "Et" and insert --et--.

Signed and Sealed this

Sixteenth Day of May, 2000

Attest:

Q. TODD DICKINSON

Attesting Officer

Director of Patents and Trademarks

SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "primer"

(xi) SEQUENCE DESCRIPTION: SEQ ID NO:1:

GGCGAAGGTT GTCAATACAG                    20

(2) INFORMATION FOR SEQ ID NO:2:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "primer"

(xi) SEQUENCE DESCRIPTION: SEQ ID NO:2:

ACCAGGACAA ACATATACAG                    20

(2) INFORMATION FOR SEQ ID NO:3:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "primer"

(xi) SEQUENCE DESCRIPTION: SEQ ID NO:3:

CCTAAGGTGT CTGCATATCA                    20

(2) INFORMATION FOR SEQ ID NO:4:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "primer"

(xi) SEQUENCE DESCRIPTION: SEQ ID NO:4:

| | |
|---|---|
| AACTGATCTA GTTCTGTACT | 20 |

(2) INFORMATION FOR SEQ ID NO:5:

(i) SEQUENCE CHARACTERISTICS:
    (A) LENGTH: 1110 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:5:

| | |
|---|---|
| AACTGCTTTT AGGCATAGGT TTTTAACTGT TTTTACTTGC CTAATAGCAT AGTTGGCCTG | 60 |
| TATAACTACT TTTGCATTCA AGAATGTGTC TTGTAGTGTA AGTTATACAG TGACTAATAC | 120 |
| CACATCCATA AATTTGTGCA ACCGAAATAG GTTGGGCACA CATACCAATA CTTTTAACCA | 180 |
| ATACTTTTAC TTATAACATT TTACAATCAT TTTATAGTAT AAAGGGAGTG ACCGAAAACG | 240 |
| GTCATGACCG AAAACGGTGT ATATAAAGCT GAACACAGCA GTTGTCTATA CCAATGGCGC | 300 |
| TATTTCACAA CCCTGAGGAA CGGCCATACA AATTGCCAGA CCTGTGCAGG ACATTGGACA | 360 |
| CCACATTGCA TGACGTTACA ATAGACTGTG TCTATTGCAG AAGGCAACTA CAACGGACAG | 420 |
| AGGTATATGA ATTTGCCTTT GGTGACTTAA ATGTAGTATA TAGGGACGGG GTACCATTAG | 480 |
| CTGCATGCCA ATCATGTATT AAATTTTATG CGAAAATACG GGAACTACGA TATTACTCAG | 540 |
| AATCGGTGTA TGCAACAACA TTAGAAACCA TAACTAATAC AAAGTTATAT GATTTATCAA | 600 |
| TAAGGTGCAT GTGTTGCCTG AAACCATTGA GTCCTGCTGA AAAACTAAGG CACCTAAATT | 660 |
| CAAAACGAAG ATTTCATAAA ATAGCAGGAA ACTTTACAGG ACAGTGTCGC CACTGCTGGA | 720 |
| CCAGTAAACG AGAGGACCGC AGACGCACAC GGCAGGAAAC ACAAGTTTAA ACTAACTATG | 780 |
| CATGGACCAA AGCCCACCGT GCAGGAAATT GTGTTAGAGT TATGTCCATG CAATGAAATA | 840 |
| GAGCCGGTCG ACCTTGTATG TCACGAGCAA TTAGGAGATT CAGACGATGA AATAGATGAA | 900 |
| CCCGACCATG CAGTTAATCA CCACCAACAT CAACTACTAG CCAGACGGGA CGAACAACAG | 960 |
| CGTCACACAA TTCAGTGTAC GTGTTGTAAG TGTAACAACC TACTGCAACT AGTAGTAGAA | 1020 |
| GCGTCGCGGG AGAACCTGCG GAACGTAGAA CTGCTGTTTA TGGACTCACT AAATTTTGTG | 1080 |
| TGTCCGTGGT GTGCAACGGA AACCCAGTAA | 1110 |

(2) INFORMATION FOR SEQ ID NO:6:

(i) SEQUENCE CHARACTERISTICS:
    (A) LENGTH: 1108 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:6:

| | |
|---|---|
| AACGGCTTTA GGCATAAAGT TTAACTGTTT TGGCTTGCCT AATAGCATAG TTGGCCAGTA | 60 |
| TAACTACTTT TGCATTCAAG AATCTGTCTG GTAGTGTAAG TTATACAGTG ACTAATACTA | 120 |

| | |
|---|---|
| CATCCATAAA TTTGTGCAAC CGAAAAAGGT TGGGCACACA TACCAATACT TTTAACCAAT | 180 |
| ACTTTTACTT ATAACATTTT ACAATTATTC TATATAAAAA AAGGGTGGGA CCGAAAACGG | 240 |
| TCACGACCGA AAACGGTGTA TATAAAGCTG AACACAGCAG TTCTCTATAC TAATGGCGCT | 300 |
| ATTTCACAAC CCTGAGGAAC GGCCATACAA ATTGCCAGAC CTGTGCAGGA CATTGGACAC | 360 |
| TACATTGCAT GACGTTACAA TAGACTGTGT CTATTGCAGA AGGCAACTAC AACGGACAGA | 420 |
| GGTATATGAA TTTGCCTTTA GTGACCTATG TGTAGTGTAT AGAGACGGGG TACCATTTGC | 480 |
| TGCATGCCAA TCATGTATTA AATTTTATGC TAAAATACGG GAACTACGAT ATTACTCGGA | 540 |
| ATCGGTGTAT GCAACTACAT TAGAAACCAT AACTAATACA AAGTTATATA ATTTATTGAT | 600 |
| AAGGTGCATG AGTTGCCTGA AACCATTGTG TCCAGCAGAA AAACTAAGGC ACCTAACAAC | 660 |
| AAAACGAAGA TTACATAAAA TAGCAGGAAA CTTTACAGGA CAGTGTCGGC ACTGCTGGAC | 720 |
| CAGTAAGCGA GAGGACCGCA GACGCATACG TCAAGAAACA CAAGTTTAAG TAACTATGCA | 780 |
| TGGACCAAAG CCCACCGTGC AGGAAATTGT GTTAGAGCTA TGTCCATACA ATGAAATACA | 840 |
| GCCGGTTGAC CTTGTATGTC ACGAGCAATT AGGAGATTCA GACGATGAAA TAGATGAACC | 900 |
| CGACCATGCA GTTAATCACC ACCAACATCT ACTACTAGCC AGACGGGACG AACAACAGCG | 960 |
| TCACAGAATT CAGTGTCTGT GTTGTAAGTG TAACAAGGCA CTGCAACTAG TAGTAGAAGC | 1020 |
| GTCGCGGGAC AACCTGCGGA CACTACAACA GCTGTTTATG GACTCACTAA ATTTTGTGTG | 1080 |
| TCCGTGGTGT GCAACTGAAA CCCAGTAA | 1108 |

(2) INFORMATION FOR SEQ ID NO:7:

(i) SEQUENCE CHARACTERISTICS:
        (A) LENGTH: 1110 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

| | |
|---|---|
| AAGTGCTTTT AGGCATGTAT TTTACCTGTT TTTACTTACC TAATAGCATA GTTGGCCTGT | 60 |
| ATAACAGCTT TTACATCCAA GAATGTGTCG TTTGGTGCAA GTTATATTTT GTGACTAATA | 120 |
| TTTTTACAGA CCTGTGTGCA ACCGAAATAG GTTGGGCAGA CATTCCTATA CTTTTATCCT | 180 |
| ATACTTTTAC TTATAACATT TTACAATCAT AATTTAAAAA AAGGGAGGCA CCGAAAACGG | 240 |
| TCACGACCGA AAACGGTGTA TATAAAACCA TGCAAAAGTT GCTTGCCCAT ACGGAATGGC | 300 |
| GCGATTTCCC AATCCTGCAG AACGGCCATA CAAATTGCCT GACCTGTGCA CGGCGCTGGA | 360 |
| CACTACATTG CACGACATTA CAATAGACTG TGTCTATTGT AAAACACAGC TACAGCAAAC | 420 |
| AGAGGTATAT GAATTTGCAT TTAGTGATTT ATTTATAGTA TATAGAAACG GGAGCCATA | 480 |
| TGCTGCATGC CAAAAATGTA TTAAATTTCA TGCTAAAGTA AGGGAACTAC GGCATTATTC | 540 |
| GAACTCGGTG TATGCAACAA CTTTGGAAAG CATAACTAAT ACCAAGTTAT ATGATTTATC | 600 |
| AATAAGGTGC ATGAGTTGCC TGAAACCATT GTGTCCAGCA GAAAAATTAA GGCATGTTAA | 660 |
| TACCAAAAGA AGATTTCACC AAATAGCAGG AAGCTATACA GGACAGTGCC GACACTGCTG | 720 |
| GACCAGCAAC CGGGAGGACC GCAGACGTAT ACGAAGAGAA ACACAAGTAT AAATATAAAT | 780 |
| ATGCATGGAC CACGGCCGAC ATTGCAAGAG ATTGTTTTAG ATTTATATCC ATACAATGAA | 840 |
| ATACAGCCGG TCGACCTTGT ATGTCACGAG CAATTAGAAG ATTCAGACAA TGAAACAGAT | 900 |
| GAACCCGACC ATGTAGTTAA TCACCAACAA CAACTACTAG CCAGACGGGA AGAACCACAG | 960 |

```
CGTCACAAAA TACAGTGTAT GTGTTGTAAG TGTAATACTA CACTGCACTT AGTAGTAGAA    1020

GCCTCACAAG AGAACCTGCG ATCTCTACTG CAGCTGTTTA TGGAGACACT GTCATTTGTG    1080

TGTCCCTGGT GTGCATCGGG AACCCAGTAA                                     1110
```

(2) INFORMATION FOR SEQ ID NO:8:

(i) SEQUENCE CHARACTERISTICS:
        (A) LENGTH: 1518 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

```
ATGGCATTGT GGCGCTCTAG CGACAACATG GTGTATTTGC CTCCCCCCTC AGTGGCGAAG     60

GTTGTCAATA CAGATGATTA CGTAACACGC ACTGGCATTT ATTACTATGC TGGTACATCT    120

AGGTTATTAA CTGTAGGCCA TCCATATTTT AAGGTCCCTA TGTCTGGGGG CCGCAAGCAG    180

GACATTCCTA AGGTGTCTGC ATATCAATAC AGGGTGTTTA GGATTTCCCT ACCTGATCCT    240

AATAAATTTA GTCTTCCTGA GTCTACATTA TATAACCCTG ATACGCAGCG ATTGGTATGG    300

GCCTGTGTTG GTGTTGAAAT AGGTAGGGGG CAGCCATTAG GTGTTGGCCT TAGTGGGCAT    360

CCATTATATA ATAGGCTAGA TGATACTGAA AATTCCCCGT TTTCCTCCAA CAAAAATCCT    420

AAGGACAGTA GGGACAATGT TTCAGTGGAC TATAAACAAA CGCAACTATG TATTATAGGC    480

TGTGTTCCTG CCATTGGAGA GCACTGGGCC AAAGGTAAAT CTTGTAAGCC TAGCAATGTG    540

CAGCCCGGGG ACTGTCCACC ATTGGAATTA GTAAATACAC CTATTCAGGA TGGCGATATG    600

ATTGATACAG GATATGGTGC TATGGACTTT AGTACATTAC AAGAAACAAA AAGCGAGGTG    660

CCTTTAGATA TATGTCAATC AGTCTGCAAA TATCCTGACT ATTTACAAAT GTCTGCAGAT    720

GTATATGGAG ACAGTATGTT CTTTTGTTTA CGTAGGGAAC AGTTATTTGC TAGGCATTTT    780

TGGAATAGAG GGGCATGGT AGGGGACACT ATACCTACTG AATTGTATAT TAAGGGCACT    840

GACATACGTG ACAGTCCTAG TAGTTATGTA TATGCCCCCT CGCCTAGTGG GTCTATGGTA    900

TCCTCAGACT CCCAGTTATT TAACAAGCCC TATTGGCTGC ACAAGGCACA GGGACACAAC    960

AATGGTATTT GTTGGCATAA TCAATTATTT CTTACTGTTG TGGATACCAC TCGCAGTACC   1020

AATTTTACTT TGTCTACTAC TACTGAATCA GCTGTACCAA ATATTTATGA TCCTAATAAA   1080

TTTAAGGAAT ATATTAGGCA TGTTGAGGAA TATGATTTGC AATTTATATT TCAGTTGTGT   1140

ACTATAACAT TGTCCACTGA TGTAATGTCC TATATACATA CTATGAATCC TGCTATTTTG   1200

GATGATTGGA ATTTTGGTGT TGCCCCTCCA CCATCTGCTA GTCTTGTAGA TACATACCGC   1260

TATCTGCAAT CAGCAGCAAT TACATGTCAA AAAGACGCCC CTGCACCTAC TAAAAAGGAT   1320

CCCTATGATG GCTTAAACTT TTGGAATGTA AATTTAAAGG AAAAGTTTAG TTCTGAACTG   1380

GACCAGTTTC CTTTAGGACG CAAATTTCTT TTACAGGCAG GTGTCCGCCG ACGACCCACT   1440

ATAGGCCCCC GTAAACGCCC TGCCACAGCA ACTACTGCAT CTACCTCTAA GCACAAACGT   1500

AAACGTGTGT CAAAGTAA                                                 1518
```

(2) INFORMATION FOR SEQ ID NO:9:

(i) SEQUENCE CHARACTERISTICS:
        (A) LENGTH: 1518 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

| | | | | | |
|---|---|---|---|---|---|
| ATGGCATTGT | GGCGAGCTAG | CGACAACATG | GTGTATTTGC | CTCCCCCCTC | AGTGGCGAAG | 60 |
| GTTGTCAATA | CAGATGATTA | TGTGACACGC | ACTGGCATGT | ATTACTATGC | TGGTACATCT | 120 |
| AGGTTATTAA | CTGTAGGCCA | TCCATATTTT | AAGGTTCCTA | TGTCTGGGGG | CCGCAAGCAG | 180 |
| GGCATTCCTA | AGGTGTCTGC | ATATCAATAC | AGAGTGTTTA | GGGTTACCTT | ACCTGATCCT | 240 |
| AATAAATTTA | GTGTTCCTGA | GTCTACATTA | TATAATCCAG | ATACACAGCG | CATGGTATGG | 300 |
| GCCTGTGTTG | GTGTTGAAAT | AGGTAGGGGG | CAGCCATTGG | GCGTTGGCCT | TAGTGGGCAT | 360 |
| CCACTATATA | ATAGGCTGGA | TGATACTGAA | AATTCCCCGT | TTTCCTCTAA | TAAAAATCCT | 420 |
| AAAGACAGTA | GGGACAATGT | TGCAGTGGAC | TGTAAACAAA | CACAGCTGTG | TATTATAGGC | 480 |
| TGTGTTCCTG | CTATTGGCGA | GCACTGGGCC | AAAGGTAAAT | CTTGTAAGCC | TACCAATGTA | 540 |
| CAACAAGGGG | ACTGTCCCCC | ATTGGAATTG | GTAAATACTC | CTATTGAGGA | TGGCGATATG | 600 |
| ATTGATACAG | GATATGGTGC | TATGGACTTT | GGTACATTAC | AAGAAACGAA | AAGCGAGGTA | 660 |
| CCTTTGGATA | TATGTCAATC | TGTTTGCAAA | TATCCTGACT | ATTTGCAAAT | GTCTGCAGAT | 720 |
| GTGTATGGAG | ACAGTATGTT | TTTTTGTTTA | CGTAGGGAAC | AGTTATTTGC | CAGGCATTTT | 780 |
| TGGAATAGGG | GAGGCATGGT | AGGGGACACT | ATTCCCACTG | ACATGTATAT | TAAGGGCACT | 840 |
| GACATTCGTG | AAACTCCTAG | TAGTTATGTG | TATGCCCCCT | CGCCTAGCGG | GTCTATGGTG | 900 |
| TCCTCTGACT | CCCAGTTATT | TAACAAGCCC | TATTGGCTGC | ACAAGGCACA | GGGACACAAC | 960 |
| AATGGTATTT | GTTGGCATAA | TCAATTATTT | CTTACCGTTG | TGGATACAAC | GCGCAGTACT | 1020 |
| AATTTTACAT | TGTCCACTAC | TACAGACTCT | ACTGTACCAG | CTGTGTATGA | TTCTAATAAA | 1080 |
| TTTAAGGAAT | ATGTTAGGCA | TGTTGAGGAA | TATGATTTGC | AGTTTATATT | TCAGTTGTGT | 1140 |
| ACTATAACAT | TATCCACTGA | TGTAATGTCA | TATATACATA | CTATGAATCC | TGCTATTTTG | 1200 |
| GATGATTGGA | ATTTTGGTGT | TGCCCCTCCA | CCATCTGCTA | GTCTTGTAGA | TACATACCGC | 1260 |
| TACCTACAAT | CAGCAGCAAT | TACATGTCAA | AAGGACGCCC | CTGCACCTGT | TAAAAAAGAT | 1320 |
| CCCTATGATG | GTCTTAACTT | TTGGAATGTG | GATTTAAAGG | AAAAGTTTAG | TTCTGAACTG | 1380 |
| GACCAATTCC | CATTAGGACG | CAAATTTCTG | TTACAGGCAG | GTGTTCGCAG | ACGGCCCACC | 1440 |
| ATAGGCCCTC | GTAAACGCAC | TGCCACTGCG | ACTACCACAT | CTACCTCTAA | ACACAAACGT | 1500 |
| AAACGTGTGT | CAAAATAA | | | | | 1518 |

(2) INFORMATION FOR SEQ ID NO:10:

(i) SEQUENCE CHARACTERISTICS:
        (A) LENGTH: 1521 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

| | | | | | |
|---|---|---|---|---|---|
| ATGGCTTTGT | GGCGGTCTAG | TGACAACACG | GTGTATTTGC | CACCCCCTTC | TGTGGCGAAG | 60 |
| GTTGTCAATA | CAGATGATTA | TGTAACACGT | ACAGGCATAT | ATTATTATGC | TGGAACGTCT | 120 |
| CGCTTATTAA | CAGTAGGGCA | TCCTTATTTT | AAGGTACCTG | TAAATGGTGG | CCGCAAGCAG | 180 |
| GAAATACCTA | AGGTGTCTGC | ATATCAGTAT | AGGGTATTTA | GGGTATCCCT | ACCTGATCCT | 240 |
| AATAAGTTTG | GCCTTCCGGA | TCCTTCCCTT | TATAATCCTG | ACACACAACG | CCTGGTATGG | 300 |
| GCCTGTATAG | GTGTGGAAAT | TGGTAGAGGC | CAGCCATTGG | GCGTTGGCGT | TAGTGGACAT | 360 |

```
CCTTTATATA ATAGGTTGGA TGATACTGAA AATTCTCATT TTTCCTCTGC TGTTAGTACA        420

CAGGACAGTA GGGACAATGT GTCTGTGGAC TATAAGCAAA CACAGTTATG TATTATAGGC        480

TGTGTTCCTG CTATGGGAGA GCACTGGGCA AAGGGCAAGG CCTGTAAGTC CACTACTGTA        540

CAACAGGGCG ATTGTCCACC ATTAGAATTA GTTAATACTG CAATTGAGGA TGGCGATATG        600

ATAGATACAG GCTATGGTGC CATGGACTTT CGTACATTGC AGGAAACCAA AAGTGAGGTA        660

CCACTAGATA TTTGCCAATC CGTGTGTAAA TATCCTGATT ATTTGCAGAT GTCTGCTGAT        720

GTATATGGGG ACAGTATGTT TTTTTGTTTG CGCAAGGAAC AGTTGTTTGC CAGGCACTTT        780

TGGAATAGAG GTGGCATGGT GGGCGACACA ATACCTTCAG AGTTATATAT TAAAGGCACG        840

GATATACGTG AGCGTCCTGG TACTCATGTA TATTCCCCTT CCCCAAGTGG CTCTATGGTC        900

TCTTCTGATT CCCAGTTGTT AATAAGCCC TATTGGTTGC ATAAGGCCCA GGACACAAT         960

AATGGCATTT GTTGGCATAA CCAGTTGTTT ATTACTGTGG TGGACACTAC ACGTAGTACT      1020

AATTTTACAT TGTCTGCCTG CACCGAAACG GCCATACCTG CTGTATATAG CCCTACAAAG      1080

TTTAAGGAAT ATACTAGGCA TGTGGAGGAA TATGATTTAC AATTTATATT TCAATTGTGT      1140

ACTATCACAT TAACTGCAGA CGTTATGGCC TACATCCATA CTATGAATCC TGCAATTTTG      1200

GACAATTGGA ATATAGGAGT TACCCCTCCA CCATCTGCAA GCTTAGTGGA CACGTATAGG      1260

TATTTACAAT CAGCAGCTAT AGCATGTCAA AAGGATGCTC CTACACCTGA AAAAAGGAT       1320

CCCTATGACG ATTTAAAATT TTGGAATGTT GATTTAAAGG AAAAGTTTAG TACAGAACTA      1380

GATCAGTTTC CTTTGGGGCG CAAATTTTTA CTACAGGTAG GGGCTCGCAG ACGTCCTACT      1440

ATAGGCCCTC GCAAACGCCC TGCGTCAGCT AAATCGTCTT CCTCAGCCTC TAAACACAAA      1500

CGGAAACGTG TGTCCAAGTA A                                                1521

(2) INFORMATION FOR SEQ ID NO:11:

(i) SEQUENCE CHARACTERISTICS:
            (A) LENGTH: 1059 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:11:

GGATCCTTCC CTTTATAATC CTGACACACA ACGCCTGGTA TGGGCCTGTA TAGGTGTGGA         60

AATTGGTAGA GGCCAGCCAT TGGGCGTTGG CGTTAGTGGA CATCCTTTAT ATAATAGATT        120

GGATGATACT GAAAATTCTC ATTTTTCCTC TGCTGTTAGT ACACAGGACA GTAGGGACAA        180

TGTGTCTGTG GACTATAAGC AAACACAGTT ATGTATTATA GGCTGTGTTC CTGCTATGGG        240

AGAGCACTGG GCTAAGGGCA AGGCCTGTAA GTCCACTCAA CAGGGCGATT GTCCACCATT        300

AGAATTAGTT AATACTGCAA TTGAGGATGG CGATATGATA GATACAGGCT ATGGTGCCAT        360

GGACTTTCGT ACATTGCAGG AAACCAAAAG TGAGGTACCA CTAGATATTT GCCAATCCGT        420

GTGTAAATAT CCTGATTATT GCAGATGTC TGCTGATGTA TATGGGACA GTATGTTTTT         480

TTGTTTGCGC AAGGAACAGT TGTTTGCCAG GCACTTTTGG AATAGAGGTG GCATGGTGGG        540

CGACACAATA CCTTCAGAGT TATATATTAA AGGCACGGAT ATACGTGAGC GTCCTGGTAC        600

TCATGTATAT TCCCCTTCCC CAAGTGGCTC TATGGTCTCT TCTGATTCCC AGTTGTTTAA        660

TAAGCCCTAT TGGTTGCATA AGGCCCAGGG ACACAATAAT GGCATTTGTT GGCATAACCA        720

GTTGTTTATT ACTGTGGTGG ACACTACACG TAGTACTAAT TTTACATTGT CTGCCTGCAC        780
```

```
CGAAACGGCC ATACCTGCTG TATATAGCCC TACAAAGTTT AAGGAATATA CTAGGCATGT      840

GGAGGAATAT GATTTACAAT TTATATTTCA ATTGTGTACT ATCACATTAA CTGCTGACGT      900

TATGGCCTAC ATCCATACTA TGAATCCTGC AATTTTGGAC AATTGGAATA TAGGAGTTAC      960

CCCTCCACCA TCTGCAAGCT TGGTGGACAC GTATAGGTAT TTACAATCAG CAGCTATAGC     1020

ATGTCAAAAG GATGCTCCTA CACCTGAAAA AAAGGATCC                            1059
```

(2) INFORMATION FOR SEQ ID NO:12:

(i) SEQUENCE CHARACTERISTICS:
        (A) LENGTH: 1095 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

```
AACGGCTTTA GGCATAAAGT TTAACTGTTT TGGCTTGCCT AATAGCATAG TTGGCCAGTA       60

TAACTACTTT TGCATTCAAG AATCTGTCTG GTAGTGTAAG TTATACAGTG ACTAATACTA      120

CATCCATAAA TTTGTGCAAC CGAAAAAGGT TGGGCACACA TACCAATACT TTTACTTATA      180

ACATTTTACA ATTATTCTAT ATAAAAAAAG GGTGGGACCG AAAACGGTCA CGACCGAAAA      240

CGGTGTATAT AAAGCTGAAC ACAGCAGTTC TCTATACTAA TGGCGCTATT TCACAACCCT      300

GAGGAACGGC CATACAAATT GCCAGACCTG TGCAGGACAT TGGACACTAC ATTGCATGAC      360

GTTACAATAG ACTGTGTCTA TTGCAGAAGG CAACTACAAC GGACAGAGGT ATATGAATTT      420

GCCTTTAGTG ACCTATGTGT AGTGTATAGA GACGGGGTAC CATTTGCTGC ATGCCAATCA      480

TGTATTAAAT TTTATGCTAA AATACGGGAA CTACGATATT ACTCGGAATC GGTGTATGCA      540

ACTACATTAG AAACCATAAC TAATACAAAG TTATATAATT TATTGATAAG GTGCATGAGT      600

TGCCTGAAAC CATTGTGTCC AGCAGAAAAA CTAAGGCACC TAACAACAAA ACGAAGATTA      660

CATAAAATAG CAGGAAACTT TACAGGACAG TGTCGGCACT GCTGGACCAG TAAGCGAGAG      720

GACCGCAGAC GCATACGTCA AGAAACACAA GTTTAAGTAA CTATGCATGG ACCAAAGCCC      780

ACCGTGCAGG AAATTGTGTT AGAGCTATGT CCATACAATG AAATACAGCC GGTTGACCTT      840

GTATGTCACG AGCAATTAGG AGATTCAGAC GATGAAATAG ATGAACCCGA CCATGCAGTT      900

AATCACCACC AACATCTACT ACTAGCCAGA CGGGACGAAC AACAGCGTCA CAGAATTCAG      960

TGTCTGTGTT GTAAGTGTAA CAAGGCACTG CAACTAGTAG TAGAAGCGTC GCGGGACAAC     1020

CTGCGGACAC TACAACAGCT GTTTATGGAC TCACTAAATT TTGTGTGTCC GTGGTGTGCA     1080

ACTGAAACCC AGTAA                                                     1095
```

(2) INFORMATION FOR SEQ ID NO:13:

(i) SEQUENCE CHARACTERISTICS:
        (A) LENGTH: 1518 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

```
ATGGCATTGT GGCGAGCTAG CGACAACATG GTGTATTTGC CTCCCCCCTC AGTGGCGAAG       60

GTTGTCAATA CAGATGATTA TGTGACACGC ACTGGCATGT ATTACTATGC TGGTACATCT      120

AGGTTATTAA CTGTAGGCCA TCCATATTTT AAGGTTCCTA TGTCTGGGGG CCGCAAGCAG      180
```

-continued

```
GGCATTCCTA AGGTGTCTGC ATATCAATAC AGAGTGTTTA GGGTTACCTT ACCTGATCCT      240

AATAAATTTA GTGTTCCTGA GTCTACATTA TATAATCCAG ATACACAGCG CATGGTATGG      300

GCCTGTGTTG GTGTTGAAAT AGGTAGGGGG CAGCCATTGG GCGTTGGCCT TAGTGGGCAT      360

CCACTATATA ATAGGCTGGA TGATACTGAA AATTCCCCGT TTTCCTCTAA TAAAAATCCT      420

AAAGACAGTA GGGACAATGT TGCAGTGGAC TGTAAACAAA CACAGCTGTG TATTATAGGC      480

TGTGTTCCTG CTATTGGCGA GCACTGGGCC AAAGGTAAAT CTTGTAAGCC TACCAATGTA      540

CAACAAGGGG ACTGTCCCCC ATTGGAATTG GTAAATACTC CTATTGAGGA TGGCGATATG      600

ATTGATACAG GATATGGTGC TATGGACTTT GGTACATTAC AAGAAACGAA AAGCGAGGTA      660

CCTTTGGATA TATGTCAATC TGTTTGCAAA TATCCTGACT ATTTGCAAAT GTCTGCAGAT      720

GTGTATGGAG ACAGTATGTT TTTTTGTTTA CGTAGGGAAC AGTTATTTGC CAGGCATTTT      780

TGGAATAGGG GAGGCATGGT AGGGGACACT ATTCCCACTG ACATGTATAT TAAGGGCACT      840

GACATTCGTG AAACTCCTAG TAGTTATGTG TATGCCCCCT CGCCTAGCGG GTCTATGGTG      900

TCCTCTGACT CCCAGTTATT TAACAAGCCC TATTGGCTGC ACAAGGCACA GGGACACAAC      960

AATGGTATTT GTTGGCATAA TCAATTATTT CTTACCGTTG TGGATACAAC GCGCAGTACT     1020

AATTTTACAT TGTCCACTAC TACAGACTCT ACTGTACCAG CTGTGTATGA TTCTAATAAA     1080

TTTAAGGAAT ATGTTAGGCA TGTTGAGGAA TATGATTTGC AGTTTATATT TCAGTTGTGT     1140

ACTATAACAT TATCCACTGA TGTAATGTCA TATATACATA CTATGAATCC TGCTATTTTG     1200

GATGATTGGA ATTTTGGTGT TGCCCCTCCA CCATCTGCTA GTCTTGTAGA TACATACCGC     1260

TACCTACAAT CAGCAGCAAT TACATGTCAA AAGGACGCCC CTGCACCTGT TAAAAAGAT      1320

CCCTATGATG GTCTTAACTT TTGGAATGTG GATTAAAGG AAAAGTTTAG TTCTGAACTG      1380

GACCAATTCC CATTAGGACG CAAATTTCTG TTACAGGCAG GTGTTCGCAG ACGGCCCACC     1440

ATAGGCCCTC GTAAACGCAC TGCCACTGCG ACTACCACAT CTACCTCTAA ACACAAACGT     1500

AAACGTGTGT CAAAATAA                                                  1518
```

(2) INFORMATION FOR SEQ ID NO:14:

(i) SEQUENCE CHARACTERISTICS:
        (A) LENGTH: 3283 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

```
AAACGTATTC CCTATTTTTT TACAGATGGC TTTGTGGCGG TCTAGTGACA ACACGGTGTA       60

TTTGCCACCC CCTTCTGTGG CGAAGGTTGT CAATACAGAT GATTATGTAA CACGTACAGG      120

CATATATTAT TATGCTGGAA CGTCTCGCTT ATTAACAGTA GGGCATCCTT ATTTTAAGGT      180

ACCTGTAAAT GGTGGCCGCA AGCAGGAAAT ACCTAAGGTG TCTGCATATC AGTATAGGGT      240

ATTTAGGGTA TCCCTACCTG ATCCTAATAA GTTTGGCCTT CCGGATCCTT CCCTTTATAA      300

TCCTGACACA CAACGCCTGG TATGGGCCTG TATAGGTGTG GAAATTGGTA GAGGCCAGCC      360

ATTGGGCGTT GGCGTTAGTG GACATCCTTT ATATAATAGG TTGGATGATA CTGAAAATTC      420

TCATTTTTCC TCTGCTGTTA GTACACAGGA CAGTAGGGAC AATGTGTCTG TGGACTATAA      480

GCAAACACAG TTATGTATTA TAGGCTGTGT TCCTGCTATG GGAGAGCACT GGGCAAAGGG      540

CAAGGCCTGT AAGTCCACTA CTGTACAACA GGGCGATTGT CCACCATTAG AATTAGTTAA      600

TACTGCAATT GAGGATGGCG ATATGATAGA TACAGGCTAT GGTGCCATGG ACTTTCGTAC      660
```

```
ATTGCAGGAA ACCAAAAGTG AGGTACCACT AGATATTTGC CAATCCGTGT GTAAATATCC    720
TGATTATTTG CAGATGTCTG CTGATGTATA TGGGGACAGT ATGTTTTTTT GTTTGCGCAA    780
GGAACAGTTG TTTGCCAGGC ACTTTTGAAA TAGAGGTGGC ATGGTGGGCG ACACAATACC    840
TTCAGAGTTA TATATTAAAG GCACGGATAT ACGTGAGCGT CCTGGTACTC ATGTATATTC    900
CCCTTCCCCA AGTGGCTCTA TGGTCTCTTC TGATTCCCAG TTGTTTAATA AGCCCTATTG    960
GTTGCATAAG GCCCAGGGAC ACAATAATGG CATTTGTTGG CATAACCAGT TGTTTATTAC   1020
TGTGGTGGAC ACTACACGTA GTACTAATTT TACATTGTCT GCCTGCACCG AAACGGCCAT   1080
ACCTGCTGTA TATAGCCCTA CAAAGTTTAA GGAATATACT AGGCATGTGG AGGAATATGA   1140
TTTACAATTT ATATTTCAAT TGTGTACTAT CACATTAACT GCAGACGTTA TGGCCTACAT   1200
CCATACTATG AATCCTGCAA TTTTGGACAA TTGGAATATA GGAGTTACCC CTCCACCATC   1260
TGCAAGCTTA GTGGACACGT ATAGGTATTT ACAATCAGCA GCTATAGCAT GTCAAAAGGA   1320
TGCTCCTACA CCTGAAAAAA AGGATCCCTA TGACGATTTA AAATTTTGGA ATGTTGATTT   1380
AAAGGAAAAG TTTAGTACAG AACTAGATCA GTTTCCTTTG GGGCGCAAAT TTTTACTACA   1440
GGTAGGGGCT CGCAGACGTC CTACTATAGG CCCTCGCAAA CGCCCTGCGT CAGCTAAATC   1500
GTCTTCCTCA GCCTCTAAAC ACAAACGGAA ACGTGTGTCC AAGTAATGTA TGTATGTGGT   1560
ATGCTGTGTA TTTATGTACT ATTACATATT TGTGTTTTTA TGTGGTATGC TTGCACACTG   1620
TTTACATATT TGTGTTTGTA TGTGGTATGC TTGCACACTG TACTGTATAT GTTTGTCCTG   1680
GTACATATTT GTGGTTGTAT GTGTATATGT TGCGTGCTAT GTGTATGTTT TAGAAGTATG   1740
TGTGTATGTA TGTTTTTGTT AATAAAGTAT GTATGGAAGT TCATTTGTG GTTGCACCCT    1800
GTGACTAAGG TGTTGTCCCT GTTTTACATA TAATAGGAGT GTGATTACCA ACATTTCCTA   1860
CATAATTTTA TGCCCTACCC TAAGGTGTGT GTATACCATC TGTAGTTTAT ACATTTATAT   1920
TTTATAGTGG GTTACCTGTA TACAGCAACG GCCATTTTGT GTGAAACCGT TTTCGGTTGC   1980
ATTTGGCTTT GTACCATCAG TTACCCTTAT AAACCTTTTG TATCAGCAAA AACATGTCCT   2040
GTAACCTAAG TTCACCTACA TACTTGGCAC TACTAACAGT TTTAGTGGCG CACCTACACT   2100
TAGTCATCAT CCTGTCCAGG TGCACTACAA CAATGCTTTG GCAACCTTAT GCACCTCCAC   2160
CCTGTCTAAT AAAGTGCTTT TAGGCATGTA TTTTACCTGT TTTTACTTAC CTAATAGCAT   2220
AGTTGGCCTG TATAACAGCT TTTACATCCA AGAATGTGTC GTTTGGTGCA AGTTATATTT   2280
TGTGACTAAT ATTTTTACAG ACCTGTGTGC AACCGAAATA GGTTGGGCAG ACATTCCTAT   2340
ACTTTTACTT ATAACATTTT ACAATCATAA TTTAAAAAAA GGGAGGCACC GAAAACGGTC   2400
ACGACCGAAA ACGGTGTATA TAAAACCATG CAAAAGTTGC TTGCCCATAC GGAATGGCGC   2460
GATTTCCCAA TCCTGCAGAA CGGCCATACA AATTGCCTGA CCTGTGCACG GCGCTGGACA   2520
CTACATTGCA CGACATTACA ATAGACTGTG TCTATTGTAA AACACAGCTA CAGCAAACAG   2580
AGGTATATGA ATTTGCATTT AGTGATTTAT TTATAGTATA TAGAAACGGG GAGCCATATG   2640
CTGCATGCCA AAAATGTATT AAATTTCATG CTAAAGTAAG GGAACTACGG CATTATTCGA   2700
ACTCGGTGTA TGCAACAACT TTGGAAAGCA TAACTAATAC CAAGTTATAT GATTTATCAA   2760
TAAGGTGCAT GAGTTGCCTG AAACCATTGT GTCCAGCAGA AAAATTAAGG CATGTTAATA   2820
CCAAAAGAAG ATTTCACCAA ATAGCAGGAA GCTATACAGG ACAGTGCCGA CACTGCTGGA   2880
CCAGCAACCG GGAGGACCGC AGACGTATAC GAAGAGAAAC ACAAGTATAA ATATAAATAT   2940
GCATGGACCA CGGCCGACAT TGCAAGAGAT TGTTTTAGAT TTATATCCAT ACAATGAAAT   3000
ACAGCCGGTC GACCTTGTAT GTCACGAGCA ATTAGAAGAT TCAGACAATG AAACAGATGA   3060
```

-continued

```
ACCCGACCAT GTAGTTAATC ACCAACAACA ACTACTAGCC AGACGGGAAG AACCACAGCG    3120

TCACAAAATA CAGTGTATGT GTTGTAAGTG TAATACTACA CTGCACTTAG TAGTAGAAGC    3180

CTCACAAGAG AACCTGCGAT CTCTACTGCA GCTGTTTATG GAGACACTGT CATTTGTGTG    3240

TCCCTGGTGT GCATCGGGAA CCCAGTAACC TGCAATGGCC AAT                     3283
```